(12) United States Patent
Pettegrew et al.

(10) Patent No.: US 7,700,074 B2
(45) Date of Patent: Apr. 20, 2010

(54) METHOD AND SYSTEM FOR DIAGNOSIS OF NEUROPSYCHIATRIC DISORDERS INCLUDING CHRONIC ALCOHOLISM

(76) Inventors: Jay W. Pettegrew, 630 S. Linden Ave., Pittsburgh, PA (US) 15208; Kanagasabai Panchalingam, 1214 Holy Cross Dr., Monroeville, PA (US) 15146

( * ) Notice: Subject to any disclaimer, the term of this patent is extended or adjusted under 35 U.S.C. 154(b) by 0 days.

(21) Appl. No.: 11/209,318

(22) Filed: Aug. 23, 2005

(65) Prior Publication Data

US 2006/0292547 A1 Dec. 28, 2006

Related U.S. Application Data

(63) Continuation-in-part of application No. 11/117,126, filed on Apr. 27, 2005, which is a continuation-in-part of application No. 10/359,560, filed on Feb. 7, 2003.

(60) Provisional application No. 60/354,323, filed on Feb. 7, 2002.

(51) Int. Cl.
| | |
|---|---|
| A61K 49/00 | (2006.01) |
| A61B 5/055 | (2006.01) |
| A61K 31/70 | (2006.01) |
| A61K 31/66 | (2006.01) |
| A61K 31/22 | (2006.01) |
| A61K 31/205 | (2006.01) |

(52) U.S. Cl. ................ 424/9.1; 424/9.3; 514/44; 514/75; 514/546; 514/556

(58) Field of Classification Search ....... 424/1.81–1.89, 424/9.1–9.3; 514/546, 556
See application file for complete search history.

(56) References Cited

U.S. PATENT DOCUMENTS

| | | | |
|---|---|---|---|
| 329,638 | A | 11/1885 | Frank |
| 394,841 | A | 12/1888 | Duisberg |
| 401,024 | A | 9/1889 | Frank |
| 622,961 | A | 4/1899 | Levinstein |
| 1,979,534 | A | 11/1934 | Ebert |
| 4,221,869 | A | 9/1980 | Vandecasteele |
| 4,346,107 | A * | 8/1982 | Cavazza et al. ............ 514/547 |
| 4,542,098 | A | 9/1985 | Vandecasteele |
| 4,642,290 | A | 2/1987 | Sih |
| 4,650,759 | A | 3/1987 | Yokozeki |
| 4,708,936 | A | 11/1987 | Kulla |
| 4,743,621 | A | 5/1988 | Cavazza |
| 4,933,156 | A | 6/1990 | Quay |
| 4,965,364 | A | 10/1990 | Marko |
| 4,996,041 | A | 2/1991 | Aral |
| 5,008,099 | A | 4/1991 | Quay |
| 5,028,538 | A | 7/1991 | Seim |
| 5,039,511 | A | 8/1991 | Quay |
| 5,066,583 | A | 11/1991 | Mueller |
| 5,156,966 | A | 10/1992 | Takahashi |
| 5,187,093 | A | 2/1993 | Kulla |
| 5,208,037 | A * | 5/1993 | Wright et al. ............ 424/473 |
| 5,231,000 | A | 7/1993 | Majocha |
| 5,276,059 | A | 1/1994 | Caughey |
| 5,358,712 | A | 10/1994 | Etange |
| 5,545,566 | A | 8/1996 | Growden |
| 5,631,168 | A | 5/1997 | Growdon |
| 5,668,117 | A | 9/1997 | Shapiro |
| 5,773,024 | A | 6/1998 | Unger |
| 5,837,219 | A | 11/1998 | Watanabe |
| 5,846,517 | A | 12/1998 | Unger |
| 5,853,985 | A | 12/1998 | Salbaum |
| 5,866,427 | A | 2/1999 | Mendelson |
| 5,879,884 | A * | 3/1999 | Peroutka ............... 435/6 |
| 5,889,055 | A | 3/1999 | Howard |
| 5,973,004 | A | 10/1999 | Howard |
| 5,976,816 | A | 11/1999 | Alkon |
| 6,037,373 | A | 3/2000 | De Simone |
| 6,066,664 | A | 5/2000 | Cavazza |
| 6,071,494 | A | 6/2000 | Unger |
| 6,080,582 | A | 6/2000 | Alkon |
| 6,107,050 | A | 8/2000 | Alkon |
| 6,114,175 | A | 9/2000 | Kiunk |

(Continued)

FOREIGN PATENT DOCUMENTS

WO WO9409371 4/1994

(Continued)

OTHER PUBLICATIONS

Pettegrew et al. (II), "Acetylk-L-Carnitine Physical-Chemical, Metabolic, and Therapeutic Properties: Relevance for its Mode of Action in Alzheimer's Disease and Geriatric Depression," Molecular Psychiatry, 5(6), 616-632 (2000).*

(Continued)

*Primary Examiner*—Lawrence E. Crane
(74) *Attorney, Agent, or Firm*—Lesavich High-Tech Law Group, P.C.; Stephen Lesavich

(57) ABSTRACT

Chronic alcoholism is a diverse and heterogeneous disorder that can be dichotomized into cognitively intact and cognitively impaired subgroups. At a molecular level, ethanol has been shown to have both acute and chronic effects on: Membrane biophysical properties, Membrane composition and metabolism, Protein phosphorylation, Lipid metabolic signaling, Lipoprotein transport of cholesterol. Actual molecular underpinnings are determined for cognitive impairment seen in some chronic alcoholism subjects including molecular/metabolic alterations of phospholipid and ganglioside metabolisms.

6 Claims, 10 Drawing Sheets

U.S. PATENT DOCUMENTS

| | | | |
|---|---|---|---|
| 6,133,259 | A | 10/2000 | Kiunk |
| 6,139,819 | A | 10/2000 | Unger |
| 6,166,077 | A | 12/2000 | De Simone |
| 6,168,776 | B1 | 1/2001 | Klunk |
| 6,175,061 | B1 | 1/2001 | Bright |
| 6,183,777 | B1 | 2/2001 | Chen |
| 6,231,834 | B1 | 5/2001 | Unger |
| 6,255,057 | B1 | 7/2001 | Gordon .................... 435/7.21 |
| 6,300,085 | B1 | 10/2001 | Alkon |
| 6,313,159 | B1 | 11/2001 | Jackson |
| 6,335,021 | B1 | 1/2002 | Cavazza |
| 6,337,197 | B2 | 1/2002 | Elssner |
| 6,346,282 | B1 | 2/2002 | Cavazza |
| 6,348,464 | B1 | 2/2002 | Jackson |
| 6,379,936 | B1 | 4/2002 | Elssner |
| 6,380,244 | B2 | 4/2002 | Martin |
| 6,380,252 | B1 | 4/2002 | De Simone |
| 6,403,056 | B1 | 6/2002 | Unger |
| 6,416,740 | B1 | 7/2002 | Unger |
| 6,417,178 | B1 | 7/2002 | Klunk |
| 6,420,599 | B2 | 7/2002 | Marzi |
| 6,479,034 | B1 | 11/2002 | Unger |
| 6,521,211 | B1 | 2/2003 | Unger |
| 6,548,047 | B1 | 4/2003 | Unger |
| 6,551,576 | B1 | 4/2003 | Unger |
| 6,576,220 | B2 | 6/2003 | Unger |
| 6,589,547 | B1 | 7/2003 | Igari |
| 6,589,948 | B1 | 7/2003 | Malfroy-Camine |
| 6,653,112 | B2 | 11/2003 | Kleber |
| 6,708,053 | B1 | 3/2004 | Brooks |
| 6,716,412 | B2 | 4/2004 | Unger |
| 6,808,720 | B2 | 10/2004 | Unger |

FOREIGN PATENT DOCUMENTS

| | | |
|---|---|---|
| WO | WO9966914 | 12/1999 |
| WO | WO03066041 | 8/2003 |
| WO | WO2004054567 | 7/2004 |

OTHER PUBLICATIONS

Garzya et al., "Evaluation of the Effects of L-Acetylcarnitine on Senile Patients Suffering from Depression," Drugs Under Experimental and Clinical Research, 16(2), 101-106 (1990).*

Pettegrew et al. (I), "31P-MRS Study of Acetyl-L-Carnitine Treatment in Geriatric Depression: Preliminary Results," Bipolar Disorders, 4(1), 61-66 (Feb. 2002).*

Fulgente et al., "Laevo-Acetylcarnitine (Nicetile®) Treatment of Senile Depression," \Clinical Trials Journal, 27(3), 155-163 (1990).*

'Casella et al., "L-Acetylcarnitine in Depressed Elderly Subjects. A Cross-Over Study vs. Placebo," Drugs Under Experimental and Clinical Research, 13(7), 417-423 (1987).*

Bella et al., "Effect of Acetyl-L-Carnitine on Geriatric Patients Suffering From Dysthymic Disorders," Int. J. Clinical Pharmacology Research, 10(6), 355-360 (1990).*

Pettegrew et al. (II), "Acetylk-L-Carnitine Physical-Chemical, Metabolic, and Therapeutic Properties: Relevance for its Mode of Action in Alzheimer's Disease and Geriatric Depression," Molecular Psychiatry, 5(6), 616-632 (2000).*

Garzya et al., "Evaluation of the Effects of L-Acetylcarnitine on Senile Patients Suffering from Depression," Drugs Under Experimental and Clinical Research, 16(2), 101-106 (1990).*

Alpha-GPC ((L-Alpha glycerylphosphorylcholine, Choline alfoscerate), on-line information published by Global Information Hub on Integrated Medicine, 2003: web address; <www.nhiondemand.com>.*

O'Neil et al. (eds.), The Merck Index, An Encyclopedia of Chemicals, Drugs, and Biologicals, 13th Edition, 2001, Merck & Co., Whitehouse Station, NJ, only pp. 16 and 312 supplied, see entry entries 86 (acetylcarnitine) and 1862 (carnitine).*

Asplund, P.T. (2001): "Intrinsic Oxygen use Kinetics of Transformed Plant Root Culture" Biotechnology Progress, vol. 17 No. 3 pp. 481-489.

Balasaraswathi, R et al (1997): "Changes in oil, sugars, and nitrogenous components during germination of sunflower seeds, *Helianthus annuus*" Plant Foods for Human Nutrition, vol. 51, No. 1, pp. 71-77.

Cabot et al.: Vasopressin, phorbol diesters and serum elicit choline glycerophospholipid hydrolysis and diacyiglycerol formation in nontransformed cells: transformed derivatives do not respond' Biochimica Et Biophysica Acta, vol. 959, 1988, pp. 46-57.

De Simone C et al.(1998): "Amerlioration of the depression of HIV-infected subjects with L acetyl carnitine therapy" Journal of Drug Development vol. 1, No. 3, pp. 163-166.

Eastmond, P. et al (2001):"Re-examining the Role of the Glyoxylate Cylce in Oilseeds" Trends in Plant Science, vol. 6. No. 2 pp. 72-77.

Eckardt, N. (2005): "Peroxisomal Citrate Synthase Provides Exit Route from Fatty Acid Metabolism in Oilseeds" Plant Cell vol. 17, No. 7. pp. 1863-1865.

Gürel, E., and K. Kazan (1998): "Development and efficient plant regeneration system in sunflower (*Helianthus annus* L.)" Tr. J. of Botany, vol. 22, pp. 381-387.

Kanfer, N; W. Pettegrew, Moossy and D.G. McCartney (1993): "Alterations of Selected Enzymes of Phospholipid Metabolism in Alzheimer's Disease Brain Tissue as Compared to Non-Alzheimer's Demented Controls," Neurochemical Research, v. 18, n. 3, pp. 33 I-334.

Klunk, W.; Chong-Jun Xu, Richard McClure, Kanagasavai Panchalingam, Jeff Stanley and Jay Pettegrew (1997): "Aggregation of B-Amyloid Peptide Is Promoted by Membrane Phospholipid Metabolites Elevated in Alzheimer's Disease Brain ," Journal of Neurochemistiy, v. 69, n. 1, pp. 266-272.

Lacey, Jeffery C and Leslie M. Loew (1983): "Phospholipid Synthesis Based on New Sequential Phosphate and Carboxylate Ester Bond Formation Steps," J. Org. Chem. v. 48, pp. 5214-5221.

Le Page-Degivry M-T et al (1990): "Involvment of endogenous abscisic acid in onset and release of hellanthus-annuus embryo dormancy" Plant Physiology, vol. 92 No. 4, pp. 1164-1168.

Mandal, Pravat K; Richard J. McClure and Jay W. Pettegrew, (2004): "Interactions of A3(1-40) with Glycerophosphocholine and Intact Erythrocyte Membranes: Fluorescence and Circular Dichroism Studies," Neurochemical Research, 29 pp. 2273-2279.

McClure, RJ.; K. Panchanlingam, J. A. Stanely and J.W. Pettegrew (2001): "Molecular Modeling of Glycerophosphocholine with an Axnyloid Beta(I-28) Peptide Fragment," Society of Neuroscience Abstracts, 27: 322.9, 2001.

Meiboom, S.(1961): "Nuclear Magnetic Resonance Study of the Proton Transfer in Water," The Journal of Chemical Physics, v.34,n. 2,pp. 375-388.

Meiboom, S; Z. Luz, and D. Gill (1957): "Proton Relaxation in Water," The Journal of Chemical Physics, v.27, n. 6, pp. 1411-1412.

Mushika et al.(1971): "A New Phosphorylating Reagent. V. The Preparation of alpha—Glycerophosphoryl Choline and its Analogues by Means of 2—Chloromethyl—4—nitrophenyl Phosphorodichloridate" Chem. Pharm. Bull.,vol. 19, No. 4.

Nasca D et al (1989): "Action of acetyl-L-carnitine in association with mianserine on depressed old people" New trends in clinical neuropharmacology. Italy. vol. 3, No. 4, pp. 225-230.

Nifant'ev et al.(1978): "Synthesis of lipids and their models from glycerol alkylene phosphites. II. Phosphatidylcholines and their analogs" J. Org. Chem. USSR, vol. 14, pp. 56-63.

Ohkatsu et al.(1988): "Synthesis and polymerization of a macromonomer derived from phosphatidicholine" Makromol. Chem., vol. 189, pp. 755-760.

Pettegrew, J.W.; P.K. Mandal, R.J. McClure and K. Panchanlingam (2003): "Glycerophosphocholine promotes aggregation of A-peptide: evidence from fluorescence, circular dichorism, and multidimensional NMR studies," University of Pittsburgh Publication, program No. 944.2.

Pettegrew, J; Kanagasabai Panchalingam, Ronald Hamilton and Richard McClure (2001): "Brain Membrane Phospholipid Alterations in Alzheimer's Disease," Neurochemical Research, v.26, n.7, pp. 771-782.

Pettegrew, JW; E. Klunk, K. Panchalingam, R.J. VcClure and 3. A. Stanely (2000): "Molecular insights into neurodevelopmental and neurodegenerative diseases, "Brain Research Bulletin, v.53, n.4, pp. 455-469.

Scuccimarra A et al.(1998): "La L-Acetilcarnitina neele sindromi dpressive di Ogni Eta L-acetylcarnitine in depressive syndromes for all ages" Gazzetta Medica Italiana, Minerva Medica. Torino, IT, vol. 147, No. 6,pp. 213-214.

Spanner et al.(1987): "The Hydrolysis of Glycerophosphocholine by Rat Brain Microsomes: Activation and Inhibition" Neurochemical Research, vol. 12, No. 2, pp. 203-206.

Sweet et al.(2002): "Psychosis in Alzheimer disease: postmortem magnetic resonance spectroscopy evidence of excess neuronal and membrane phospholipid pathology" Neurobiology of Aging, vol. 23, 2002, pp. 547-553.

Volz et al(1998): "31P magnetic resonance spectroscopy in the frontal lobe of major depressed patients" European Archives of Psychiatry and Clinical Neuroscience. vol. 248, No. 6, December pp. 289-295.

Yanker, B; Lawrence Duffy and Daniel Kirschner (1990): "Neurotrophic and neurotoxic effects of amyloid beta protein: reversal by tachykinin neuropeptides," Science, v.250, n.4978, pp. 279-283.

Yildiz A et al (2001): "P.nuclear magnetic resonance spectroscopy findings in bipolar illness: A meta-analysis" Psychiatry Research-Neuroimaging. vol. 106, No. 3, May 30, 2001, pp. 181-191.

International Search Report PCT/US2004/016,750, Jan. 21, 2005.

International Search Report PCT/US2006/016,095, Nov. 22, 2006.

Goldstein G; Pettegrew J W; Comelisu J; "Molecular studies of cognition in alcoholism," Alcoholism: Clinical and Experimental Research, vol. 29, No. 5s, May 2005 p. 101A, XP009083852 RSA Abstract No. 566.

Pettegrew, J. W. et al. "Metabolic effects of chronic alcoholism" A 31P-1H MRS Study XP002433988, Database Bios Online, Biosciences Information service, Database accession No. PREV200100552020 abstract, Nov. 10, 2001.

Mason G F; Bendszus M; Meyerhoff D J; Hetherington H P; Schwiensburg B; Ross B; Taylor M; Krystal J H; Magentic Resonance Spectroscopic Studies of Alchoholism; From Heavy Drinking to Alcohol Dependence and Back Again. Alcoholism: Clinical and Experimental Research, pp. 150-158, XP002433976. V. 29; Jan. 2005.

Estllaei M R; Matson G.B; Payne G S; Leach M O; Fein G; Meyerhoff D J; "Effects of Chronic Alcohol Consumption on Broad Phosphollpid Signal in Human Brains: An In Vivo 31P MRS Study" Alcoholism: Clinical and Experimental Research, vol. 25, No. 1, Jan. 2001, pp. 89-97, XP002433977.

Bonsch D; Greifenbarg V; Bayerlein K; Biermann T; Reulbach U; Hillemacher T; Kornhuber J; Bleich S; "alpha-synuclien Protein Levels are Increased in Alcoholic Patients and Are Linked to Cravilng" Alcoholism: Clinical and Experimental Research, vol. 29, No. 5, May 2005, pp. 763-765, XP002433978.

Meyerhoff D; Mackay S; Sappey-Mariner D; Dlecken R; Calabrese G; Dillon WP; Wlener M W; Fien G;"Effect of Chronic Alcohol Abuse and HIV Infection on Brain Phosphorus Metabolites" Alcoholism: Clinical and Experimental Research, vol. 19, No. 3, Jul. 1995, pp. 685-692, XP00243379.

Meyerhoff D; Blumfield R; Truran D; Chao L L; Rothlind J; Studhome C; Wiener M W: "Effects of Heavy Drinking, Bringe Drinking and Family History of Alchoism on Regional Brain Metabolites" Alcoholism: Clinical and Experimental Research, vol. 28, No. 4. Apr. 2004, pp. 650-661, XP002433980.

Partial PCT Search Report PCT/2006/032,749 , Apr. 6, 2007.

* cited by examiner

FIG. 3A
Entry
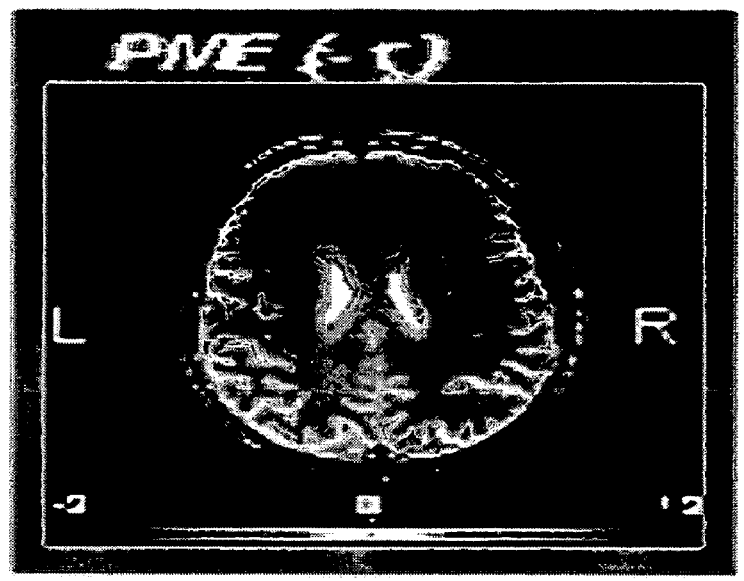
12 Weeks

FIG. 3B
Entry
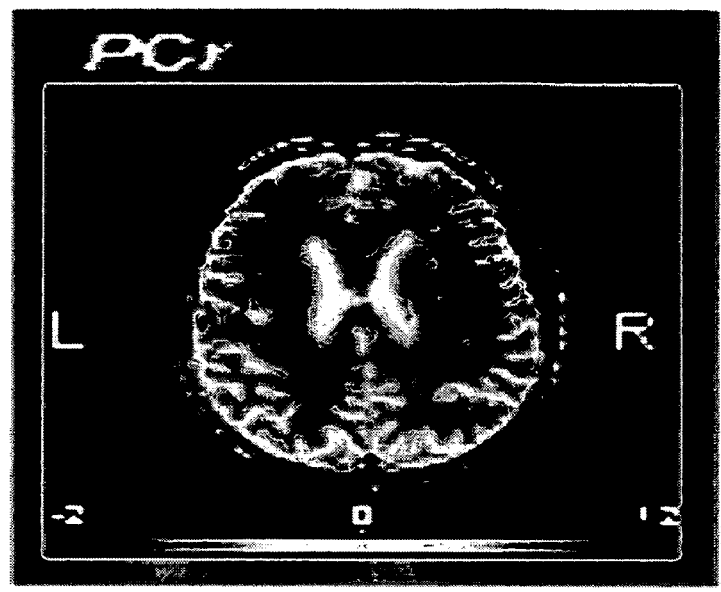
12 Weeks
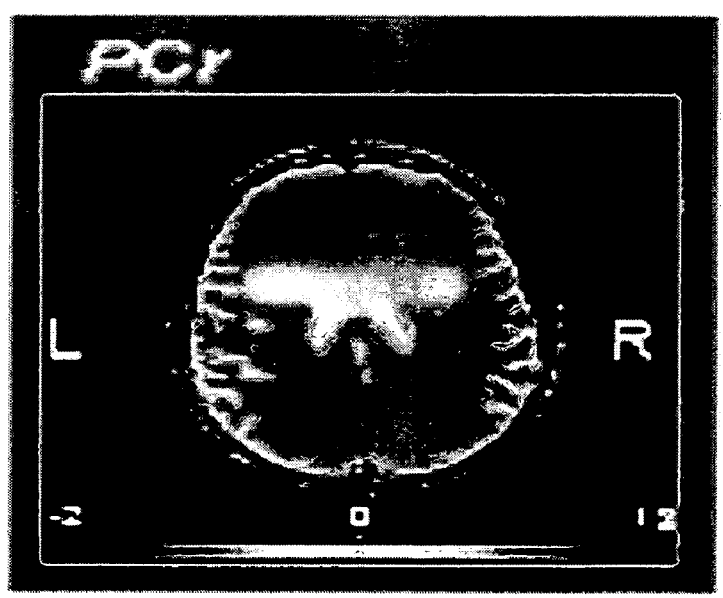

COGNITIVELY IMPAIRED (N=4) VS
COGNITIVELY UNIMPAIRED (N=5)

CORRELATIONS -- MRS METABOLITES VS.
NEUROPSYCHOLOGICAL SCORES (N=9)

Cognitively Impaired (N=19) vs
Cognitively Unimpaired (N=16)

CORRELATIONS -- MRS METABOLITES
VS. NEUROPSYCHOLOGICAL SCORES (N=35)

Middle Age Smokers (N=8)
Nicotine vs. Placebo Patch

METHOD AND SYSTEM FOR DIAGNOSIS OF NEUROPSYCHIATRIC DISORDERS INCLUDING CHRONIC ALCOHOLISM

CROSS REFERENCES TO RELATED APPLICATIONS

This application is a Continuation-In-Part (CIP) of U.S. application Ser. No. 11/117,126, filed Apr. 27, 2005, which is a CIP of U.S. application Ser. No. 10/359,560, filed Feb. 7, 2003, which claims priority to U.S. Provisional application No. 60/354,323, filed Feb. 7, 2002, contents of all of which are incorporated by reference.

FIELD OF THE INVENTION

The present invention relates to methods adapted for diagnosis of the progression of neuropsychiatric disorders, specifically chronic alcoholism disease.

BACKGROUND OF THE INVENTION

The clinical response to antidepressant treatment in later life follows a variable temporal response, with a median time to remission of 12 weeks. Newer antidepressants still demonstrate a disturbing side-effect profile in this fragile patient population. Thus, there is a need for the development of newer antidepressants. One such candidate is acetyl-L-carnitine (ALCAR), a molecule that is naturally present in human brain demonstrating only few side effects.

Seven parallel, double-blind, placebo-controlled studies have examined ALCAR efficacy in various forms of geriatric depression. Phosphorus magnetic resonance spectroscopy ($^{31}$P MRS) directly provides information on membrane phospholipid and high-energy phosphate metabolism in defined, localized brain regions. Although in vivo $^{31}$P MRS studies in major depression are limited, there is evidence of altered high-energy phosphate and membrane phospholipid metabolism in the prefrontal and basal ganglia regions. Increased levels of precursors of membrane phospholipids [i.e., increased phosphomonoesters (PME) levels] in the frontal lobe of major depressed subjects compared to controls was reported. Other researchers also observed higher PME levels in bipolar subjects in their depressive phase compared with the euthymic state. In terms of high-energy phosphates, reduced levels of adenosine triphosphate (ATP) have been observed in both the frontal and basal ganglia of major depressed subjects. The level of the high-energy phosphate buffer, phosphocreatine (PCr), was lower in severely depressed subjects compared with mildly depressed subjects. Accordingly, the relationship between membrane phospholipid and high-energy phosphate metabolism as assessments of beneficial results in the treatment of depression are recognized.

Epidemiology of Depressive Disorders

Depressive disorders (i.e., major depression, dysthymia, bipolar disorder) are among the most common and disabling medical conditions throughout the world. For example, about 9.5% of the U.S. adult population will suffer from a form of depression during any given year which is approximately 18.8 million people. In addition, 16-18% of women and 10% of men (3-4 million) will experience some form of depression. The lifetime risk for depression is approximately 15-20% regardless of gender.

When one episode of depression is experienced, there is a 50% likelihood of recurrent episodes. When a second episode of depression occurs, there is a 80-90% likelihood of recurrent episodes and 75% of depressive disorders are recurrent.

It is estimated 20% of depressed individuals will attempt suicide and 6% will be successful. 75% of those committing suicide have a depressive disorder. The rate of successful suicide is four times greater in men.

About 10% of people with depression also will experience episodes of mania. Bipolar depressive episodes usually last longer, have a greater likelihood of psychotic features, and convey a greater risk of suicide. Bipolar disorder may be misdiagnosed as depression resulting in inappropriate treatment that may worsen the disease progression and outcome.

Depression is a acotraveler with a number of other medical and psychiatric conditions and numerous medications can cause depressive symptoms.

The prevailing dogma concerning the pathophysiology of depressive disorders (major depression, dysthymia, bipolar disorder) is that of an altered neurotransmitter receptor and many studies have been conducted to find such an alteration. To date, there has been no demonstration of an alteration in the binding site for any of the targeted neurotransmitters. Another problem with the altered neurotransmitters receptor dogma is that although the tricyclic antidepressants and selective neurotransmitter reuptake inhibitor drugs quickly enter brain and bind to their targeted sites, the clinical therapeutic effect does not occur for 4-6 weeks even though the onset of side effects is immediate.

Studies by Samuel Gershon over the years, since early 1950, have questioned the concepts of the established modes of action of antidepressants and those of the etiology of affective disorders.

In the early 50's a number of papers appeared suggesting that lithium not only had anti-manic properties but that it also exhibited anti-depressant and prophylactic activity in depression. These observations were confirmed by the controlled studies carried out by Schou et al. in Denmark and Prien et al. in Australia. This tended to indicate that perhaps a single neurotransmitter and a single receptor site would not qualify as the full explanation of their effects. In 1961, Gershon published a report in the Lancet on the psychiatric sequelae of organo-phosphorus insecticides in an exposed human population. Thus a role for acetylcholine in contributing to the production of major depressive disorder (MDD) was presented. This added to the complexity of current theories. In the 1970's an antidepressant Ludiomil was marketed with the effect of being a specific norepinephrine (NE) uptake inhibitor and thus exerting its effect by this route. This was an effective agent and was taken off the market because of other adverse effects (AE). In 1970 Gershon and colleagues carried out a number of experiments with synthesis inhibitors in patients undergoing treatment with different antidepressants and showed that only the inhibition of serotonin synthesis and not NE synthesis interfered with antidepressant outcomes.

These experiments demonstrated that a single transmitter or a single receptor could not account for therapeutic activity and clearly suggested other mechanisms are involved relating to membrane effects and second messenger systems. Antidepressant use has now clearly been associated with treatment emergent mania and the induction of rapid cycling in affective disorder patients (Tamada et al., 2004).

In addition to the concerns that have been established with the more classic bipolar I (BPI) type, much controversy surrounds the use of antidepressants in bipolar II (BPII) depression, a growing population.

Antidepressant induced cycle acceleration has been reported to be more likely in BPII patients than in BPI (Altshuler et al., 1995; Joffe et al., 2002; Benazzi, 1997; Henry et al., 2001; Ramasubbu, 2001).

The data has increasingly shown the need for the use of effective antidepressants but at the same time has produced data indicating the need for caution with the agents available. These effective antidepressants cause both the risk of switch into mania and the even more serious effect of rapid cycling of the affective disorder and an alteration of the frequency and severity of episodes.

A different conceptual approach has been the subject of almost 3 decades of research by Jay W. Pettegrew. This concept is that there is nothing structurally wrong with neurotransmitter receptors, but the receptors are in a membrane environment that has altered molecular structure and dynamics. It is these membrane alterations that alter the functional dynamics of neurotransmitter receptors which in turn alters their physiological function. Dr. Pettegrew was one of the first to demonstrate alterations in membrane molecular dynamics in living cells obtained from patients with neuropsychiatric disorders. Alterations were similarly demonstrated in cells obtained from patients with depression (Pettegrew et al., 1979c; Pettegrew et al., 1980a; Pettegrew et al., 1981a; Pettegrew et al., 198; Pettegrew et al., 1979b; Pettegrew et al., 1980b; Pettegrew et al., 1981b; Pettegrew et al., 1982b; Pettegrew et al., 1987b; Pettegrew et al., 1993b; Pettegrew et al., 1990c; Pettegrew et al., 1993a; Pettegrew et al., 1990b). Lithium was shown to correct the membrane dynamic alterations observed in depressive patients.

Given the rather striking changes in membrane molecular dynamics, Dr. Pettegrew turned to investigate alterations in membrane metabolism (Pettegrew et al., 1978; Pettegrew and Minshew, 1981; Pettegrew et al., 1982a; Glonek et al., 1982a) (Pettegrew et al., 1979a; Glonek et al., 1982b; Cohen et al., 1984; Pettegrew et al., 1986; Pettegrew et al., 1987a; Pettegrew et al., 1988a; Pettegrew et al., 1988b; Pettegrew et al., 1990a; Pettegrew et al., 1991; Keshavan et al., 1991; Kanfer et al., 1993; Pettegrew et al., 1994; Singh et al., 1994; Pettegrew et al., 1995; Klunk et al., 1996; Geddes et al., 1997; Klunk et al., 1998; Pettegrew et al., 2001; Keshavan et al., 2003; Sweet et al., 2002) and again significant alterations were observed in several neuro-psychiatric disorders including major depressive disorder (Pettegrew et al., 2002). Again, lithium was shown to correct the alteration in membrane metabolism observed in patients with depression.

Concerns About Current Classes of Antidepressants in Depressive Disorders

Concerns have been accumulating on the widespread use of all the current classes of antidepressants. This is reflected in the recently published North American based treatment guidelines (Grunze et al., 2002; Hirschfeld et al., 2002); including those of the APA (Sachs et al., 2000). These recommendations have voiced considerable limitations and a conservative attitude to their use, recommending use be restricted to severe bipolar depressions (Goodwin & Jamison, 1990; Murray & Lopez, 1996; Bostwick & Pankratz, 2000). The recommendations go on to suggest that if antidepressants are used they should be withdrawn as early as possible; thus we are now seeing a shift away from both the use of the current classes of antidepressants and recommendations for their long term use since they are associated with the following problems.

1. The risk for induced mania. There is now established a considerable risk of antidepressant induced manic switching and/or rapid cycling. This is seen in both short term and long term exposures. For example with selective reuptake inhibitors (SRIs) clinical samples demonstrate length of switch that are not minimal, that is 15 to 27%. The authors of a number of review articles on this topic suggest that the real rates are around 40% for tricyclic antidepressants (TCAs) and 20% with new SRI antidepressants. Substance abuse has been shown to be a major predictor of antidepressant-induced mania.

2. The risk of suicide in bipolar depressed patients. This risk is in and of itself a significant issue of concern. An analysis of SRIs and other novel antidepressants submitted to the FDA totaling nearly 20 thousand cases showed that there was no significant difference in completed or attempted suicides between patients on antidepressants and placebo treated groups. Simply stated, it appears that antidepressants as a group have not been shown to adequately reduce suicide rates. However, the data on lithium is in contrast to this with a very well established finding of its prophylactic effects against suicidality in a variety of diagnostic categories.

3. Antidepressant efficiency in treating bipolar depression. Prophylactic studies with antidepressants are not robust in the treatment of depressive episodes in bipolar disorders. Again, in contrast, the evidence of efficiency in treating bipolar depression with mood stabilizers is much higher (e.g., lithium and lamotrogine).

4. The potential value of other antidepressant classes. Based on this extensive new information as to the cautions that need to be employed in the use of the standard and SRI antidepressant classes, there is an urgent need for new classes of antidepressant thymoleptics. One such agent, ALCAR has a body of literature that supports the possibility of its therapeutic value in a number of depressive categories.

In view of its unique biochemical effects on the nervous system and its stabilizing effects on membrane functions, ALCAR's antidepressant activity may indeed provide a unique opportunity to address the above-described concerns. Since ALCAR is a natural substance and has been shown to have antidepressant properties without significant side effects and without the potential to induce mania, it is a logical new therapeutic approach.

ALCAR has been shown to have beneficial effects on age-related neurodegenernation and brain energetic stress providing a rationale for its use in Major Depressive Disorder (MDD). In European clinical trials to date, ALCAR has demonstrated antidepressant activity in MDD subjects without significant side effects (Villardita et al., 1983; Tempesta et al., 1987; Nasca et al., 1989; Bella et al., 1990; Fulgente et al., 1990; Garzya et al., 1990).

Overview of Biological Findings in Major Depressive Disorder

MDD has been shown to be associated with changes in: (1) neurotransmitter systems such as serotonin, acetylcholine, and noradrenergic; (2) membranes (e.g., composition, metabolism, biophysical parameters, signal transduction, and ion transport); (3) brain energy metabolism; and (4) brain structure. Computed tomography (CT) and magnetic resonance imaging (MRI) studies in subjects with non-demented, geriatric, major depressive disorder suggest neurodegenerative changes are associated with vascular risk factors (Krishnan, 1993). Beyond brain structural changes, there is evidence from fimctional neuroimaging studies for molecular, metabolic, and physiologic brain changes suggestive of energetic stress in subjects with MDD. Positron emission tomography (PET) and single photon emission computed tomography (SPECT) studies show a reduced fluorodeoxyglucose metabolic rate (rCMRg) (Buchsbaum et al., 1986) and reduced regional cerebral blood flow (rCBF) (Schlegel et al., 1989) in the basal ganglia and a decrease in rCMRg and rCBF in the frontal lobes of subjects with MDD (Mayberg et al., 1994). Of the neuroimaging methods, $^{31}$P and $^{1}$H magnetic resonance spectroscopic imaging ($^{31}$P-$^{1}$H MRSI) studies provide direct information on membrane phospholipid and high-energy phosphate metabolism ($^{31}$P MRSI) as well as a marker for neuronal structural and metabolic integrity ($^{1}$H MRSI). $^{31}$P and $^{1}$H MRS studies of subjects with MDD indicate alterations in high-energy phosphate and membrane phospholipid metabolism in basal ganglia and prefrontal cortex (Moore et al., 1997a; Charles et al., 1994; Pettegrew et al. 2002).

Neuromorphometric Changes in MDD

Neuroimaging studies have enhanced our understanding of the pathophysiology of MDD. MRI studies provide neuromorphometric correlates of MDD (reviewed by Botteron & Figiel, 1997). MRI studies of third ventricle size in major depression give mixed results; Coffey et al. (1993) report no difference in ventricle size and Rabins et al. (1991) report increased third ventricle size in subjects with MDD compared with controls. Brain MRI subcortical white matter hyperintensities have been reported in the basal ganglia, periventricular region, and frontal lobe of elderly depressed (Coffey et al., 1988; Figiel et al., 1989; Rabins et al., 1991). There have been reports of decreased volumes of the basal ganglia in MDD; Husain et al. (1991) found reduced volume in the putamen, Krishnan et al. (1993) found reduced volume in the caudate, and Dupont et al. (1995) found reduced volume in the caudate, lenticular nucleus, and thalamus. Coffey et al. (1993) report an approximately 7% reduction in bilateral frontal lobe volume in subjects with MDD.

These studies reveal neurodegenerative change in MDD. Other as yet unknown molecular and metabolic factors could predispose to both depression and the neuromorphometric changes associated with it.

Magnetic Resonance Spectroscopy Studies of Major Depressive Disorder (MDD)

While there are several MRS studies in bipolar disorder (reviewed by Moore & Renshaw, 1997b), there are only two $^{31}$P MRS studies (Kato et al., 1992; Moore et al., 1997a) and one $^{1}$H MRS analysis of MDD (Charles et al., 1994). Kato et al. (1992), using a coronal slice DRESS $^{31}$P MRS protocol, examined the frontal cortex of 12 subjects (age 35.3∀12.1 years) with MDD, 10 subjects (age 42∀8.6 years) with bipolar disorder and 22 control subjects (age 36.1∀1.5 years). Although the pH and PME levels were significantly higher in euthymic MDD subjects compared with euthymic bipolar subjects, no significant differences were found for $^{31}$P MRS parameters of MDD subjects compared with control subjects. A study by Moore et al. (1997a) using a $^{31}$P MRS ISIS protocol, measured $^{31}$P metabolites in a 45 cm$^3$ voxel containing the bilateral basal ganglia in 35 unmedicated subjects (age 37.2∀lain 8.5 years) with MDD and 18 control subjects (age 38.2∀9.9 years). There was a 16% reduction in ATP (β-ATP peak) in the MDD subjects. The PCr/Pi ratio of MDD subjects compared with control subjects did not change. This study indicates that an abnormality in basal ganglia high-energy phosphate metabolism is associated with MDD. A $^{1}$H MRS study by Charles et al. (1994), using a combination of the STEAM technique for spatial lipid suppression and 1D CSI for additional spatial localization of the basal ganglia and thalamus, examined seven subjects with MDD (age range 63-76, mean=71.4 years) compared with ten control subjects (age range 65-75, mean=68.9 years). The subjects with MDD were medication free for two (1 subject) or three (6 subjects) weeks. The authors report an increase in the TMA MRS peak in the basal ganglia of MDD subjects and subsequent drop in the trimethlyamine (TMA) peak in four subjects after treatment. We have recently observed an increase in PME and a decrease in PCr in two subjects with MDD (Pettegrew et al., unpublished results).

Molecular and Metabolic Effects of Alcar

There is neuroimaging evidence for neurodegeneration and a reduction in energy metabolite levels and RCBF in MDD. These findings provide a rationale for the use of ALCAR in MDD as there is a considerable body of research that indicates that ALCAR has a positive modulating influence on membrane structure, function and metabolism, energy metabolism, and the physiology and metabolism of neurotrophic factors. There also is clinical evidence that ALCAR is beneficial in the treatment of neurodegenerative disorders as well as normal aging-related processes and the treatment of geriatric depression. A thorough review of the possible CNS actions of ALCAR has appeared (Calvani & Carta, 1991; Pettegrew et al., 2000). What follows is a brief review of the metabolic, physiologic, behavioral, and clinical roles for ALCAR.

Alcar's Effect on Energy Metabolism

ALCAR has been shown to exert a beneficial effect on brain metabolism after energetic stresses. In a canine model of complete, global cerebral ischemia and reperfusion, ALCAR treated animals exhibited significantly lower neurological deficit scores (p=0.0037) and more normal cerebral cortex lactate/pyruvate ratios than did vehicle-treated control animals (Rosenthal et al., 1992). In a rat cyanide model of acute hypoxia, increased rate of phosphatidic acid formation, possibly reflecting increased phospholipase C activity was observed and spatial navigation performance in a Morris task was impaired. Chronic treatment with ALCAR attenuated the cyanide-induced behavioral deficit but had no effect on energy-dependent phosphoinositide metabolism suggesting ALCAR affected free fatty acid metabolism by increasing the reservoir of activated acyl groups involved in the reacylation of membrane phospholipids (Blokland et al., 1993). In a canine model employing 10 minutes of cardiac arrest followed by restoration of spontaneous circulation for up to 24 hours, ALCAR eliminated the reperfusion elevation of brain protein carbonyl groups which reflect free radical-induced protein oxidation (Liu et al., 1993). In a rat streptozotocin-induced model of brain hypoglycemia, ALCAR attenuated both the streptozotocin-induced impairment in spatial discrimination learning and decrease in hippocampal choline acetyltransferase activity (Prickaerts et al., 1995). A deficiency in ALCAR has been shown to be a cause for altered nerve myo-inositol content, Na$^+$-K$^+$-ATPase activity, and motor conduction velocity in the streptozotocin-diabetic rat (Stevens et al., 1996). Finally, sparse-fur mice have a deficiency of hepatic ornithine transcarbamylase resulting in congenital hyperammonemic with elevated cerebral ammonia and glutamine and reduced cerebral cytochrome oxidase activity and a reduction in cerebral high-energy phosphate levels. ALCAR treatment increased cytochrome oxidase subunit I MRNA, and restored both cytochrome oxidase activity and the levels of high-energy phosphates (Rao et al., 1997). Our studies of hypoxia in Fischer 344 rats demonstrate ALCAR's beneficial effect on brain membrane phospholipid and high-energy phosphate metabolism (Pettegrew et al., unpublished results.

Alcar's Effect on Membrane Composition, Structure, and Dynamics

ALCAR has been shown to effect membrane structure and function in a number of different systems. ALCAR administration affects the inner mitochondrial membrane protein composition in rat cerebellum (Villa et al., 1988), increases human erythrocyte membrane stability possibly by interacting with cytoskeletal proteins (Arduini et al., 1990), increases human erythrocyte cytoskeletal protein-protein interactions (Butterfield & Rangachari, 1993), and alters the membrane dynamics of human erythrocytes in the region of the glycerol backbone of membrane phospholipid bilayers (Arduini et al., 1993).

Alcar's Enhancement of Nerve Growth Factor Activity

A number of studies have demonstrated that ALCAR enhances the neurotrophic activity of nerve growth factor (NGF). ALCAR increases NGF binding in aged rat hippocampus and basal forebrain (Angelucci et al., 1988), increases NGF receptor expression in rat striatum, and increases choline acetyltranferase activity in the same area (De Simone R. et al., 1991), enhances PC12 cells response to NGF (Taglialatela et al., 1991), increases the level of NGF receptor (P75NGFR) mRNA (Taglialatela et al., 1992), increases choline acetyltransferase activity and NGF levels in adult rats following total fimbria-fornix transection (Piovesan et al., 1994; 1995), and enhances motomeuron survival in rat facial nucleus after facial nerve transection (Piovesan et al., 1995).

Influence of Alcar on Cholinergic and Serotonergic Neurotransmitter Systems

ALCAR has some cholinergic activity (Fritz, 1963; Tempesta et al., 1985), possibly because it shares conformational properties with acetylcholine (Sass & Werness, 1973). This is interesting as acetylcholine may play an important role in the chronobiological organization of the human body (Morley & Murrin, 1989; Wee & Turek, 1989), mediating also some effects of light on the circadian clock (Wee & Turek, 1989). Acetylcholine is implicated in the regulation of the hypothalamic-pituitary-adrenal (HPA) axis (Mueller et al., 1977; Risch et al., 1981) and cholinomimetics are effective on the HPA axis (Janowsky et al., 1981; Risch et al., 1981). ALCAR also seems to interfere with the serotonergic system (Tempesta et al., 1982; 1985). There is ample evidence supporting a reduction in serotonergic activity in depression (Ashcroft et al., 1966; Asberg et al., 1976; Cochran et al., 1976; Traskman et al., 1981; Stanley & Mann, 1983); although these results have not always been confirmed (Bowers, 1974; Murphy et al., 1978). The efficacy of 5-HTP also has been reported in involutional depression (Aussilloux et al., 1975). Moreover the selective serotonin reuptake inhibitors (SSRI) antidepressants increase serotonergic transmission and are currently widely used in treating MDD (Aberg-Wistedt et al., 1982; Stark & Hardison, 1985). Serotonin plays an important role in the regulation of circadian rhythms (Kordon et al., 1981; Leibiwitz et al., 1989) and there is consistent evidence that it affects cortisol secretion (Imura et al., 1973; Krieger, 1978; Meltzer et al., 1982).

Alcar's Effect on Aging-related Metabolic Changes

ALCAR has been demonstrated to reverse aging-related changes in brain ultrastructure, neurotransmitter systems, membrane receptors, mitochondrial proteins, membrane structure and metabolism, memory, and behavior. ALCAR restores the number of axosomatic and giant bouton vesicles in aged rat hippocampus (Badiali et al., 1987), reduces aging-related lipofuscin accumulation in prefrontal pyramidal neurons and hippocampal CA3 neurons in rats (Kohjimoto et al., 1988; Amenta et al., 1989), and reduces aging-related changes in the rat hippocampal mossy fiber system (Ricci et al., 1989). ALCAR reduces the age-dependent loss of glucocorticoid receptors in rat hippocampus (Ricci et al., 1989), attenuates the age-dependent decrease in NMDA receptors in rat hippocampus (Fiore & Rampello, 1989; Castorina et al., 1993; 1994; Piovesan et al., 1994; and reviewed by Castorina & Ferraris, 1988), and reduces age-related changes in the dopaminergic system of aging mouse brain (Sershen et al., 1991). Age-related changes in mitochondria also are reduced by ALCAR. ALCAR increases cytochrome oxidase activity in rat cerebral cortex, hippocampus, and striatum (Curti et al., 1989), restores to normal reduced transcripts of mitochondrial DNA in rat brain and heart but not liver (Gadaleta et al., 1990), increases cytochrome oxidase activity of synaptic and non-synaptic mitochondria (Villa & Gorini, 1991), reverses age-related reduction in the phosphate carrier and cardiolipin levels in heart mitochondria (Paradies et al., 1992), reverses age-related reduction in cytochrome oxidase and adenine nucleotide transferase activity in rat heart by modifying age-related changes in mitochondrial cardiolipin levels (Paradies et al., 1994; 1995), and reverses age-related alteration in the protein composition of the inner mitochondrial membrane (Villa et al., 1988). ALCAR also increases synaptosomal high-affinity choline uptake in the cerebral cortex of aging rats (Curti et al., 1989; Piovesan et al., 1994), increases choline acetyltransferase activity in aged rat striatum (De Simone R. et al., 1991; Taglialatela et al., 1994), modulates age-related reduction in melatonin synthesis (Esposti et al., 1994), reverses the age-related elevation in free and esterified cholesterol and arachidonic acid (20:4) in rat plasma (Ruggiero et al., 1990), and increases PCr and reduces lactate/pyruvate and sugar phosphate levels in adult and aged rat brain (Aureli et al., 1990). Age-related changes in NGF are reduced by ALCAR: ALCAR increases NGF receptor expression in rat striatum (De Simone R. et al., 1991) and in PC12 cells (Castorina et al., 1993); enhances the effect of NGF in aged dorsal root ganglia neurons (Manfridi et al., 1992); exerts a neurotrophic effect in three month old rats after total fimbria transection (Piovesan et al., 1994); and increases NGF levels in aged rat brain (Taglialatela et al., 1994). ALCAR has been shown in aged rats to modulate synaptic structural dynamics (Bertoni-Freddari et al., 1994) and improve measures of behavior (Angelucci, 1988; Kohjimoto et al., 1988) as well as memory (Barnes et al., 1990; Caprioli et al., 1990; 1995). ALCAR has been reported to normalize the pituitary-adrenocortical hyperactivity in pathological brain aging (Nappi et al., 1988; Ghirardi et al., 1994). We have reported that ALCAR improves standardized clinical measures and measures of membrane phospholipid and high-energy phosphate metabolism in subjects with Alzheimer's disease (AD) measured by in vivo $^{31}P$ MRS (Pettegrew et al., 1995). We now have data in a rat hypoxia model which demonstrate that ALCAR has more beneficial effects on aged rats (30 months) than on adolescent (1 month) or adult (12 months) animals (Pettegrew et al., unpublished results).

Antidepressant Effects of Alcar

In European clinical trials, ALCAR has been shown to have significant antidepressant activity in geriatric depressed subjects with minimal or no side effects (Villardita et al., 1983; Tempesta et al., 1987; Nasca et al., 1989; Bella et al., 1990; Fulgente et al., 1990; Garzya et al., 1990; Gecele et al., 1991). Villardita et al. (1983) reported a double-blind ALCAR/placebo study of 28 subjects (18 males, 10 females; 72.3∀7.3 years). Sixteen subjects were treated with ALCAR (1.5 gm/day; baseline HDRS=26.3∀3.3) and 12 patients were treated with placebo (baseline HDRS=26.6∀3.2) for 40 days.

By day 40, the ALCAR treated subjects showed significant improvement (p<0.001) in the Hamilton Depressive Rating Scale (HDRS) but the placebo treated subjects did not. There were no side effects to ALCAR. Tempesta et al. (1987) in an open label, cross over study of 24 subjects over the age of 70 years, all of whom were nursing home residents, reported ALCAR (2 gm/day) to be highly effective in reducing HDRS scores, especially in subjects with more severe clinical symptoms. Again there were no reported ALCAR side effects. In a simple blind ALCAR/placebo study of 20 subjects (10 ALCAR treated subjects; 62.5∀5.7 years, 8 males, 2 females, baseline HDRS=44.9∀3.1 and 10 placebo treated subjects; 62.5∀5.3 years, 8 males, 2 females, baseline HDRS=43.9∀2.8), Nasca et al. (1989) demonstrated a significant improvement in the HDRS scores of ALCAR treated subjects at day 40 of treatment (p<0.001). There was no improvement in the placebo treated group. Similar significant beneficial effects of ALCAR on the HDRS were observed in randomized, double-blind, ALCAR/placebo studies of Garzya et al. (1990) (28 subjects; ages 70-80 years; ALCAR 1.5 gm/day), Fulgente et al. (1990) [60 subjects; 70-80 years; ALCAR 3.0 gm/day; baseline HDRS (ALCAR=25; placebo=23); day 60 HDRS (ALCAR=12; placebo=22); p # 0.0001], and Bella et al. (1990) [60 subjects, 60-80 years, ALCAR 3.0 gm/day; baseline HDRS (ALCAR=22; placebo=21); day 60 HDRS (ALCAR=11; placebo=20); p # 0.0001]. ALCAR was well tolerated in these studies even at the higher dosages. A double-blind, ALCAR/placebo study by Gecele et al. (1991) (30 subjects, 66-79 years, ALCAR 2 gm/day) not only showed a significant improvement in the HDRS of ALCAR treated subjects (p<0.001) but a significant reduction in both mean cortisol levels (p<0.001) as well as 12 am (p<0.001) and 4 pm (p<0.01) cortisol levels.

Since acetyl-L-carnitine (ALCAR) is a natural substance and has been shown to have antidepressant properties without significant side effects and without the potential to induce mania, it is a logical new therapeutic approach.

Cognition in Alcoholism

Chronic alcoholism is a diverse and heterogeneous disorder that can be dichotomized into cognitively intact and cognitively impaired subgroups. At a molecular level, ethanol has been shown to have both acute and chronic effects on: Membrane biophysical properties, Membrane composition and metabolism, Protein phosphorylation, Lipid metabolic signaling, Lipoprotein transport of cholesterol. There may be molecular underpinnings for cognitive impairment seen in some chronic alcoholism subjects.

There is a long-standing need within the medical community for a diagnostic tool for assessing cognitive impairment seen in some chronic alcoholism subjects. Such a tool would be extremely useful in the development of treatments that delay or prevent cognitive impairment due to chronic alcoholism.

REFERENCES

Aberg-Wistedt A, Ross S B, Jostell K G & Sjoqvist B. A double-blind study of a 5-HT uptake inhibitor in endogenous depression. *Acta Psychiatr Scand* 66:66-82, 1982.

Aitchison J. *The Statistical Analysis of Compositional Data*, Chapter 7, London: Chapman and Hall, 1986, Alexopoulos G S, Meyers B S, Young R C, Kakuma T, Feder M, Einhom A & Rosendahl E. Recovery in geriatric depression. *Arch Gen Psychiatry* 53:305-312, 1996.

Altshuler L L, Post R M, Leverich G S, Mikalauskas K, Rosoff A and Ackerman L (1995) Antidepressant-induced mania and cycle acceleration: A controversy revisited.[see comment]. *Am. J. Psychiatry* 152, 1130-1138.

Amenta F, Ferrante F, Lucreziotti R, Ricci A & Ramacci M T. Reduced lipofuscin accumulation in senescent rat brain by long-term acetyl-L-carnitine treatment. *Arch Gerontol Geriatr* 9:147-153, 1989.

Angelucci L, Ramacci M T, Taglialatela G, Hulsebosch C, Morgan B, Werrbach-Perez K & Perez-Polo R. Nerve growth factor binding in aged rat central nervous system: effect of acetyl-L-carnitine. *J Neurosci Res* 20:491-496, 1988.

Arduini A, Gorbunov N, Arrigoni-Martelli E, Dottori S, Molajoni F, Russo F & Federici G. Effects of L-carnitine and its acetate and propionate esters on the molecular dynamics of human erythrocyte membrane. *Biochim Biophys Acta* 1146: 229-235, 1993.

Arduini A, Rossi M, Mancinelli G, Belfiglio M, Scurti R, Radatti G & Shohet S B. Effect of L-carnitine and acetyl-L-carnitine on the human erythrocyte membrane stability and deformability. *Life Sci* 47:2395-2400, 1990.

Asberg M, Traskman L & Thoren P. 5-HIAA in the cerebrospinal fluid: A biochemical suicide predictor? *Arch Gen Psychiatry* 33:1193-1197, 1976.

Ashcroft G W, Crawford T B B, Eccleston D, Sharman D F, MacDougall E J, Stanton J B & Binns J K. 5-Hydroxyindole compounds in the cerebrospinal fluid of patients with psychiatric or neurological disease. *Lancet* ii: 1049-1052, 1966.

Aureli T, Miccheli A, Ricciolini R, Di Cocco M E, Ramacci M T, Angelucci L, Ghirardi O & Conti F. Aging brain: Effect of acetyl-L-carnitine treatment on rat brain energy and phospholipid metabolism. A study by $^{31}P$ and $^{1}H$ NMR spectroscopy. *Brain Res* 526:108-112, 1990.

Aussilloux C H, Castelnau D, Chiariny J F & Frassinet M. A propos d'une autre voie d'abord des etats depressifs les precurseurs de la serotonine. *J Med (Montpellier)* 10:23-25, 1975.

Badiali D L, Bonvicini F, Bianchi D, Bossoni G & Laschi R. Ultrastructural aspects of ageing rat hippocampus and effects of L-acetyl-carnitine treatment. *Drugs Under Experimental & Clinical Research* 13:185-189, 1987.

Barnes C A, Markowska A L, Ingram D K, Kametani H, Spangler E L, Lemken V J & Olton D S. Acetyl-L-carnitine. 2: Effects on learning and memory performance of aged rats in simple and complex mazes. *Neurobiol Aging* 11:499-506, 1990.

Beekman A T, Deeg D J, van Tilburg T, Smit J H, Hooijer C & van Tilburg W. Major and minor depression in later life: a study of prevalence and risk factors. *J Affective Disorders* 36:65-75, 1995.

Bella R, Bondi R, Raffaele R & Pennisi G. Effect of acetyl-L-carnitine on geriatric patients suffering from dysthymic disorders. *Int J Clin Pharmacol Res* 10:355-360, 1990.

Benazzi F (1997) Antidepressant-associated hypomania in outpatient depression: a 203-case study in private practice. *J. Affective Disord.* 46, 73-77.

Bertoni-Freddari C, Fattoretti P, Casoli T, Spagna C & Casell U. Dynamic morphology of the synaptic junctional areas during aging: the effect of chronic acetyl-L-carnitine administration. *Brain Res* 656:359-366, 1994.

Birken D L & Oldendorf W H. N-Acetyl-L-aspartic acid: A literature review of a compound prominent in $^{1}H$-NMR spectroscopic studies of brain. *Neurosci Biobehav Rev* 13:23-31, 1989.

Blazer D G, Hughes D C & George L K. The epidemiology of depression in an elderly community population. *Gerontologist* 27:281-287, 1987.

Blokland A, Bothmer J, Honig W & Jolles J. Behavorial and biochemical effects of acute central metabolic inhibition: effects of acetyl-L-carnitine. *Eur J Pharmacology* 235:275-281, 1993.

Borson S. Psychiatric problems in the mentally ill elderly. In: *Comprehensive Textbook of Psychiatry*, edited by H I Kaplan & B J Sadock, 6th edition, p. 2586, 1995.

Borson S, Barnes R A, Kukull W A, Okimoto J T, Veith R C, Inui T S, Carter W & Raskind M A. Symptomatic depression in elderly medical outpatients.I.Prevalence, demography, and health service utilization. *J Am Geriatr Soc* 34:341-347, 1986.

Bostwick J M & Pankratz V S. Affective disorders and suicide risk. *Am. J. Psychiatry*, 157:1925-1932, 2000.

Botteron K N & Figiel G S. The neuromorphometry of affective disorders. In: *Brain Imaging in Clinical Psychiatry*, edited by K R R Krishnan & P M Doraiswamy. New York: Marcel Dekker,Inc., 1997, p. 145-184.

Bowers M B. Lumbar CSF 5-hydroxyindoleacetic acid and homovanillic acid in affective syndromes. *J Nerv Ment Dis* 158:325-330, 1974.

Buchsbaum M S, Wu J, DeLisi L E, Holcomb H, Kessler R, Johnson J, King A C, Hazlett E, Langston K & Post R M. Frontal cortex and basal ganglia metabolic rates assessed by positron emission tomography with [$^{18}$F]2-deoxyglucose in affective illnness. *J Affective Disord* 10:137-152, 1986.

Burnell E E, Cullis P R & de Kruijff B. Effects of tumbling and lateral diffusion on phosphatidylcholine model membrane $^{31}$P-NMR lineshapes. *Biochim Biophys Acta* 603:63-69, 1980.

Butterfield D A & Rangachari A. Acetylcarnitine increases membrane cytoskeletal protein-protein interactions. *Life Sci* 52:297-303, 1993.

Callahan C M, Hui S L, Nienaber N A, Musick B S & Tierney W M. Longitudinal study of the depression and health services use among elderly primary care patients. *J Am Geriatr Soc* 42:833-838, 1994.

Calvani M & Carta A. Clues to the mechanism of action of acetyl-L-carnitine in the central nervous system. *Dementia* 2:1-6, 1991.

Caprioli A, Ghirardi O, Ramacci M T & Angelucci L. Age-dependent deficits in radial maze performance in the rat: effect of chronic treatment with acetyl-L-carnitine. *Progress In Neuro-Psychopharmacology & Biological Psychiatry* 14:359-369, 1990.

Caprioli A, Markowska A L & Olton D S. Acetyl-L-Carnitine: chronic treatment improves spatial acquisition in a new environment in aged rats. *J Gerontology Series A, Biological Sciences & Medical Sciences* 50:B232-B236, 1995.

Castorina M, Ambrosini A M, Giuliani A, Pacifici L, Ramacci M T & Angelucci L. A cluster analysis study of acetyl-L-carnitine effect on NMDA receptors in aging. *Exp Gerontol* 28:537-548, 1993.

Castomia M, Ambrosini A M, Pacific L, Ramacci M T & Angelucci L. Age-dependent loss of NMDA receptors in hippocampus, striatum, and frontal cortex of the rat: prevention by acetyl-L-carnitine. *Neurochem Res* 19:795-798, 1994.

Cerdan S, Subramanian V H, Hilberman M, Cone J, Egan J, Chance B & Williamson J R. 31P NMR detection of mobile dog brain phospholipids. *Magn Reson Med* 3:432-439, 1986.

Charles H C, Lazeyras K K, Krishnan K R R, Boyko O B, Payne M & Moore D. Brain choline in depression: In vivo detection of potential pharmacodynamic effects of antidepressant therapy using hydrogen localized spectroscopy. *Prog Neuropsychopharmacol Biol Psychiatry* 18:1121-1127, 1994.

Cochran E, Robin E & Grote S. Regional serotonin levels in brain: a comparison of depressive suicide and alcoholic suicides with control. *Biol Psychiatry* 11:283-294, 1976.

Coffey C E, Figiel G S & Djang W T. Leukoencephalopathy in elderly depressed patients referred for ETC. *Biol Psychiatry* 24:143-161, 1988.

Coffey C E, Wilkerson W E, Weiner R D, Parashos I A, Djang W T, Webb M C, Figiel G S & Spritzer C E. Quantative cerebral anatomy in depression. *Arch Gen Psychiatry* 50:7-16, 1993.

Cohen M M, Pettegrew J W, Kopp S J, Minshew N and Glonek T (1984) P-31 nuclear magnetic resonance analysis of brain: normoxic and anoxic brain slices. *Neurochem. Res.* 9, 785-801.

Conwell Y. Suicide in elderly patients. In: *Diagnosis and Treatment of Depression in Late Life*, edited by L S Schneider, C F Reynolds & B D Lebowitz. 1996, p. 397-418.

Cullis P R & DeKruijff B. Lipid polymorphism and the functional roles of lipids in biological membranes. *Biochim Biophys Acta* 559:399-420, 1979.

Curti D, Dagani F, Galmozzi M R & Marzatico F. Effect of aging and acetyl-L-carnitine on energetic and cholinergic metabolism in rat brain regions. *Mech Ageing Develop* 47:39-45, 1989.

de Beer R & van Ormondt D. Analysis of NMR data using time domain fitting procedures. In: *NMR Basics, Principles and Progress*, edited by P Diehl & E G Fluck. New York: Springer-Verlag, 1992, p. 201-258.

de Graaf A A, vanDijk J E, & Bovee W M M J. QUALITY: quantification improvement by converting lineshapes to the Lorentzian type. *Magn Reson Med* 13:343-357, 1990.

de Kruijff B, Rietveld A & Cullis P R. $^{31}$P-NMR studies on membrane phospholipids in microsomes, rat liver slices and intact perfused rat liver. *Biochim Biophys Acta* 600:343-357, 1980.

de Kruijff B, Verkley A J, van Echteld C J A, Gerritsen W J, Mombers C, Noordam P C & De Gier J. The occurance of lipidic particles in lipid bilayers as seen by $^{31}$P NMR and freeze-fracture electron-microscopy. *Biochim Biophys Acta* 555:200-209, 1979.

De Simone R., Ramacci M T & Aloe L. Effect of acetyl-L-carnitine on forebrain cholinergic neurons of developing rats. *Int J Develop Neurosci* 9:39-46, 1991.

Desu M M & Raghavarao D. *Sample Size Methodology*. New York: Academic Press, 1990, page 30.

Dew M A, Reynolds C F, Houck P R, Hall M, Buysse D J, Frank E & Kupfer D J. Temporal profiles of the course of depression during treatment: Predictors of pathways toward recovery in the elderly. *Arch Gen Psychiatry* 54:1016-1024, 1997.

Dupont R M, Jernigan T L, Heindel W, Butters N, Shafer K, Wilson T, Hesselink J & Gillin J C. Magnetic resonance imaging and mood disorders. *Arch Gen Psychiatry* 52:747-755, 1995.

Efron B & Tibshirani R. *An Introduction to the Bootstrap*. London: Chapman and Hall, 1993.

Esposti D, Mariani M, Demartini G, Lucini V, Fraschini F & Mancia M. Modulation of melatonin secretion by acetyl-L-carnitine in adult and old rats. *J Pineal Res* 17 :132-136, 1994.

Figiel G S, Coffey C E & Weiner R D. Brain magnetic resonance imaging in elderly depressed patients receiving electroconvulsive therapy. *Convulsive Ther* 5:26-34, 1989.

Fiore L & Rampello L. L-acetylcarnitine attenuates the age-dependent decrease of NMDA-sensitive glutamate receptors in rat hippocampus. *Acta Neurol* 11:346-350, 1989.

Folstein M, Folstein S & McHugh P R. Mini-mental state: A practical method for grading the cognitive state of patients for the clinician. *J Psychiatr Res* 12:189-198, 1975.

Frahm J, Bruhn H, Gyngell M L, Merboldt K D, Hanicke W & Sauter R. Localized proton NMR spectroscopy in different regions of the human brain in vivo. Relaxation times and concentrations of cerebral metabolites. *Magn Reson Med* 11:47-63, 1989.

Frasure-Smith N, Lesperance F & Talajic. Depression following myocardial infarction. *JAMA* 270:1819-1825, 1993.

Frasure-Smith N, Lesperance F & Talajic M. Depression and 18-month prognosis after myocardial infarction. *Circulation* 91:999-1005, 1995.

Fritz I B. Carnitine and its role in fatty acid metabolism. *Adv Lipid Res* 1:285-333, 1963.

Fulgente T, Onofrj M, Del Re M L, Ferracci F, Bazzano S, Ghilardi M F & Malatesta G. Laevo-acetylcarnitine (Nicetile[R]) treatment of senile depression. *Clin Tri J* 27:155-163, 1990.

Gadaleta M N, Petruzzella V, Renis M, Fracasso F & Cantatore P. Reduced transcription of mitochondrial DNA in the senescent rat. Tissue dependence and effect of L-carnitine. *Eur J Biochem* 187:501-506, 1990.

Garzya G, Corallo D, Fiore A, Lecciso G, Petrelli G & Zotti C. Evaluation of the effects of L-acetylcarnitine on senile patients suffering from depression. *Drugs Exptl Clin Res* 16:101-106, 1990.

Gecele M, Francesetti G & Meluzzi A. Acetyl-L-carnitine in aged subjects with major depression: Clinical efficacy and effects on the circadian rhythm of cortisol. *Dementia* 2:333-337, 1991.

Geddes J W, Panchalingam K, Keller J N and Pettegrew J W (1997) Elevated phosphocholine and phosphatidyl choline following rat entorhinal cortex lesions. *Neurobiol. Aging* 18, 305-308.

Geriatric Pyschiatry Allicance. Diagnosis and treatment of late-life depression: making a difference. Monograph produced through a grant from Pfizer, Inc., 1996.

Ghirardi O., Caprioli, O., Ramacci, M. T. and Angelucci, L., Effect of long-term Acetyl-L-carnitine on stress-induced analygesia in the aging rat. *Exp Gerontol* 29:569-574, 1994.

Glonek T, Kopp S J, Kot E, Pettegrew J W and Cohen M M (1982a) P-31 nuclear magnetic resonance analysis of brain. The perchloric acid extract spectrum. *Trans. Am. Soc. Neurochem.* 13, 143.

Glonek T, Kopp S J, Kot E, Pettegrew J W, Harrison W H and Cohen M M (1982b) P-31 nuclear magnetic resonance analysis of brain: The perchloric acid extract spectrum. *J Neurochem.* 39, 1210-1219.

Gonzalez-Mendez R, Litt L, Koretsky A P, von Colditz J, Weiner M W & James T L. Comparison of $^{31}$P NMR spectra of in vivo rat brain using convolution difference and saturation with a surface coil. Source of the broad component in the brain spectrum. *J Magn Reson* 57:526-533, 1984.

Goodwin F K & Jamison K R. Manic Depressive Illness, New York, N.Y., Oxford University Press, 1990.

Grunze H, Kasper S, Goodwin G, et al., World federation of societies of biological psychiatry (WFSBP) guidelines for biological treatment of bipolar disorder, part 1: treatment of bipolar depression. *World J. Biol. Pschiatry,* 3:115-124, 2002.

Harris G J, Barta P E, Peng L W, Lee S, Brettschneider P D, Shah A, Henderer J D, Schlaepfer T E & Pearlson G D. MR volume segmentation of gray matter and white matter using manual thresholding: Dependence on image brightness. *AJNR* 15:225-230, 1994.

Harris G J, Rhew E H, Noga T & Pearlson G D. User-friendly method for rapid brain and CSF volume calculation using transaxial MRI images. *Psychiatry Res Neuroimaging* 40:61-68, 1991.

Haselgrove J C, Subramanian J H, Christen R & Leigh P N. Analysis of in vivo NMR spectra. *Rev Magn Reson Med* 2:167-222, 1987.

Henry C, Sorbara F, Lacoste J, Gindre C and Leboyer M (2001) Antidepressant-induced mania in bipolar patients: identification of risk factors.[see comment]. *J Clin. Psychiatry* 62, 249-255.

Herschfeld R M A, Bowden C L, Gitlin M J, et al., Practice guideline for the treatment of patients with bipolar disorder (revision). *Am. J. Psychiatry,* 59:1-50, 2002.

Husain M M, McDonald W M, Doraiswamy P M, Figiel G S, Na C, Escalona P R, Boyko O B, Nemeroff C B & Krishnan K R R. A magnetic resonance imaging study of putamen nuclei in major depression. *Psychiatry Res* 40:95-99, 1991.

Imura H, Naki Y & Yoshimi T. Effects of 5-hydroxytryptophan (5-HTP) on growth hormone and ACTH release in man. *J Clin Endocrinol Metab* 36:204-206, 1973.

International Conference. Draft consensus guideline: Statistical principles for clinical trials. *International conference on harmonisation of technical requirements for registration ofpharmaceuticals for human use*, ICH Steering Committee, 1997.

Janowsky D S, Risch S C, Judd L L & et al. Cholinergic supersensitivity in affective disorder patients: Behavioral and neuroendocrine observations. *Psychopharmacol Bull* 17:129-132, 1981.

Joffe R T, MacQueen G M, Marriott M, Robb J, Begin H and Young L T (2002) Induction of mania and cycle acceleration in bipolar disorder: effect of different classes of antidepressant. *Acta Psychiatr. Scand.* 105, 427-430.

Kanfer J N, Pettegrew J W, Moossy J and McCartney D G (1993) Alterations of selected enzymes of phospholipid metabolism in Alzheimer's disease brain tissue as compared to non-Alzheimer's disease controls. *Neurochem. Res.* 18, 331-334.

Kato T, Takahashi S, Shioiri T & Inubushi T. Brain phosphorus metabolism in depressive disorders detected by phosphorus-31 magnetic resonance spectroscopy. *J Affective Disord* 26 :223-230, 1992.

Keshavan M S, Anderson S, Beckwith C, Nash K, Pettegrew J & Krishnan KRR. A comparison of stereology and segmentation techniques for volumetric measurements of brain ventricles. *Psychiatry Res Neuroimaging* 61:53-60, 1995.

Keshavan M S, Beckwith C, Bagwell W, Pettegrew J W & Krishnan K R R. An objective method for edge detection in MRI morphometry. *Eur Psychiatry* 9:205-207, 1994.

Keshavan M S, Pettegrew J W, Panchalingam K, Kaplan D and Bozik E (1991) Phosphorus 31 magnetic resonance spectroscopy detects altered brain metabolism before onset of schizophrenia. *Arch. Gen. Psychiatry* 48, 1112-1113.

Keshavan M S, Stanley J A, Montrose D M, Minshew N J and Pettegrew J W (2003) Prefrontal membrane phospholipid metabolism of child and adolescent offspring at risk for schizophrenia or schizoaffective disorder: an in vivo 31P MRS study. *Molecular Psychiatry* 8, 316-323.

Kilby P M, Bolas N M & Radda G K. 31P-NMR study of brain phospholipid structures in vivo. *Biochim Biophys Acta* 1085:257-264, 1991.

Klunk W E , Xu C J, McClure R J, Panchalingam K, Stanley J A & Pettegrew J W. Aggregation of beta-amyloid peptide is promoted by membrane phospholipid metabolites elevated in Alzheimer's disease brain. *J Neurochem* 97:266-272, 1997.

Klunk W E, Panchalingam K, McClure R J, Stanley J A and Pettegrew J W (1998) Metabolic alterations in postmortem Alzheimer's disease brain are exaggerated by Apo-E4. *Neurobiol. Aging* 19, 511-515.

Klunk W E, Xu C, Panchalingam K, McClure R J and Pettegrew J W (1996) Quantitative $^1$H and $^{31}$P MRS of PCA extracts of postmortem Alzheimer's disease brain. *Neurobiol. Aging* 17, 349-357.

Kohjimoto Y, Ogawa T, Matsumoto M, Shirakawa K, Kuwaki T, Yasuda H, Anami K, Fujii T, Satoh H & Ono T. Effects of acetyl-L-carnitine on the brain lipofuscin content and emotional behavior in aged rats. *Japanese J Pharmacology* 48:365-371, 1988.

Kordon C, Hery M, Szafarcyk A, Ixart A & Assenmacher I. Serotonin and the regulation of neuroendocrine rhythms. *J Physiol* 77:489-496, 1981.

Krieger D. Factors influencing the circadian periodicity of ACTH and corticosteriods. *Med Clin North Am* 62:87-91, 1978.

Krishnan K R, McDonald W M, Doraiswamy P M, Tupler L A, Husain M, Boyko O B, Figiel G S & Ellinwood E H, Jr. Neuroanatomical substrates of depression in the elderly. *Eur Arch Psychiatry Clin Neurosci* 243:41-46, 1993.

Krishnan K R R. Neuroanatomic substrates of depression in the elderly. *J Geriatric Psychiatry Neurol* 6:39-58, 1993.

Lebowitz B D, Pearson J L, Schneider L S, Reynolds C F, Alexopoulos G S, Bruce M L, Conwell Y, Katz I R, Meyers B S, Morrison M F, Mossey J F, Neiderehe g & Parmelee P A. Diagnosis and treatment of depression in late-life: Consensus statement update. *JAMA* 278:1186-1190, 1997.

Leibiwitz S F, Weiss G F, Walsh U A & Viswanath D. Medial hypotalamic serotonin: Role in circadian patterns of feeding and macronutrient selection. *Brain Res* 503:132-140, 1989.

Lim K O, Pauly J, Webb P, Hurd R & Macovski A. Short T E phosphorus spectroscopy using a spin-echo pulse. *Magn Reson Med* 32:98-103, 1994.

Little J T, Reynolds C F, Dew M A, Frank E, Begley A E, Miller M D, Comes C L, Mazumdar S, Perel J M & Kupfer D J. How common is treatment-resistant geriatric depression. *Am J Psychiatry* (under editorial review) 1998.

Liu Y, Rosenthal R E, Stark-Reed P & Fiskum G. Inhibition of postcardiac arrest brain protein oxidation by acetyl-L-carnitine. *Free Radical Biol Med* 15:667-670, 1993.

Luyten P R, Bruntink G, Sloff F M, Vermeulen J W A H, van der Heijden J I, den Hollander J A & Heerschap A. Broadband proton decoupling in human $^{31}$P NMR spectroscopy. *NMR in Biomedicine* 1:177-183, 1989.

Manfridi A, Forloni G L, Arrigoni-Martelli E & Mancia M. Culture of dorsal root ganglion neurons from aged rats: effects of acetyl-L-carnitine and NGF. *Int J Develop Neurosci* 10:321-329, 1992.

Mason R P, Trumbore M W & Pettegrew J W. Membrane interactions of a phosphomonoester elevated early in Alzheimer's disease. *Neurobiol Aging* 16:531-539, 1995.

Mayberg H S, Lewis P J, Regenold W & Wagner H N. Paralimbic hypoperfusion in unipolar depression. *J Nucl Med* 35:929-934, 1994.

McIlwain H & Bachelard H S. *Biochemistry and the central nervous system.* 5$^{th}$ edition, Edinburgh: Churchill Livingstone, 1985, p. 42.

McNamara R, Arias-Mendoza F & Brown T R. Investigation of broad resonances in $^{31}$P NMR spectra of the human brain in vivo. *NMR Biomedicine* 7:237-242, 1994.

Meltzer H Y, Wiita B, Tricou B J, Simonovic M & Fang V S. Effects of serotonin precursors and serotonin agonists on plasma hormone levels. *Adv Biochem Psychopharmacol* 34:117-140, 1982.

Merboldt K D, Chien D, Hanicke W, Gyngell M L, Bruhn H & Frahm J. Localized $^{31}$P NMR spectroscopy of the adult human brain in vivo using stimulated-echo (STEAM) sequences. *J Magn Reson* 89:343-361, 1990.

Meyers B. Psychiatric intervention to improve primary care diagnosis and treatment of depression. *Am J Geriatric Psychiatry* 4:S91-S95, 1996.

Michaelis T, Merboldt K D, Bruhn H & Frahm J. Absolute concentrations of metabolites in the adult human brain in vivo: Quantification of localized proton NMR spectra. *Radiology* 187:219-227, 1993.

Miller B L, Moats R A, Shonk T, Ernst T, Woolley S & Ross B D. Alzheimer's disease: Depiction of increased cerebral myo-inositol with proton MR spectroscopy. *Radiology* 187:433-437, 1993.

Moore C M, Christensen J D, Lafer B, Fava M & Renshaw P F. Lower levels of nucleoside triphosphate in the basal ganglia of depressed subjects: A phosphorous-31 magnetic resonance spectroscopy study. *Am J Psychiatry* 154:116-118, 1997a.

Moore C M & Renshaw P F. Magnetic resonance spectroscopy studies of affective disorders. In: *Brain Imaging in Clinical Psychiatry*, edited by K R R Krishnan & P M Doraiswamy. New York: Marcel Dekker, 1997b, p. 185-213.

Morley B J & Murrin L C. AF64 depletes hypothalamic high affinity choline uptake and disrupts the circadian rhythm of locomotor activity without altering the density of nicotinic acetylcholine receptors. *Brain Res* 504:238-246, 1989.

Mueller E E, Nistico G & Scapagnini U. Brain neurotransmitters and the regulation of anterior pituitary function. In: *Neurotransmitters and Anterior Pituitary Function*, edited by E E Mueller, G Nistico & U Scapagnini. New York: Academic Press, 1977.

Murphy D L, Campbell I & Costa J L. Current studies of the indoleamine hypothesis of the affective disorders. In: *Psychopharmacolgy: A Generation of Progress*, edited by M A Lipton, A DiMascio & K F Killam. New York: Raven Press, 1978, p. 1235-1248.

Murphy E J, Bates T E, Williams S R, Watson T, Brindle K M, Rajagopalan B & Radda G K. Endoplasmic reticulum: The major contributor to the PDE peak in hepatic $^{31}$P-NMR spectra at low magnetic field strengths. *Biochim Biophys Acta* 1111:51-58, 1992.

Murphy E J, Rajagopalan B, Brindle K M & Radda G K. Phospholipid bilayer contribution to $^{31}$P NMR spectra in vivo. *Magn Reson Med* 12:282-289, 1989.

Murray C J L & Lopez A D (editors). The Global Burden of Disease, Cambridge, Mass., Harvard University Press, 1996.

Nappi G & et al. Acetyl-L-carnitine normalizes pituitary-adrenocortical hyperactivity in pathological ageing brain. *Med Sci Res* 16:291-292, 1988.

Nardini M, Bonelli G, Iannuccelli M, Calvani M, Magnani N & Mancuso M. Assessment of L-acetylcarnitine efficacy against fluoxetine in the depressive syndrome. In preparation, 1998.

Nasca D, Zurria G & Aguglia E. Action of acetyl-L-carnitine in association with mianserine on depressed old people. *New Trends Clin Neuropharmacology* 3:225-230, 1989.

Oxman T E, Barrett J E, Barrett J & Gerber P. Symptomatology of late-life minor depression among primary care patients. *Psychosomatics* 31:174-180, 1990.

Paradies G, Ruggiero F M, Gadaleta M N & Quagliariello E. The effect of aging and acetyl-L-carnitine on the activity of the phosphate carrier and on the phospholipid composition in rat hear mitochondria. *Biochim Biophys Acta* 1103:324-326, 1992.

Paradies G, Ruggiero F M, Petrosillo G, Gadaleta M N & Quagliariello E. Effect of aging and acetyl-L-carnitine on the activity of cytochrome oxidase and adenine nucleotide translocase in rat heart mitochondria. *FEBS Letters* 350:213-215, 1994.

Paradies G, Ruggiero F M, Petrosillo G, Gadaleta M N & Quagliariello E. Carnitine-acylcarnitine translocase activity in cardiac mitochondria from aged rats: the effect of acetyl-L-carnitine. *Mechanisms of Ageing & Development* 84:103-112, 1995.

Petroff O A C, Prichard J W, Behar K L, Alger J R, den Hollander J A & Shulman R G. Cerebral intracellular pH by $^{31}P$ nuclear magnetic resonance spectroscopy. *Neurology* 35:781-788, 1985.

Pettegrew J W, Glonek T, Baskin F and Rosenberg R N (1978) Phosphorus-31-31 NMR of neuroblastoma clonal lines. Effect of cell cycle stage and dibutyryl cyclic AMP. *Proc. 14th Midwest Regional Am. Chem. Soc.* 45.

Pettegrew J W, Glonek T, Baskin F and Rosenberg R N (1979a) Phosphorus-31 NMR of neuroblastoma clonal lines: effect of cell confluency state and dibutyryl cyclic AMP. *Neurochem. Res.* 4, 795-801.

Pettegrew J W, Keshavan M S, Panchalingam K, Strychor S, Kaplan D B, Tretta M G and Allen M (1991) Alterations in brain high-energy phosphate and membrane phospholipid metabolism in first-episode, drug-naive schizophrenics. A pilot study of the dorsal prefrontal cortex by in vivo phosphorus 31 nuclear magnetic resonance spectroscopy. *Arch. Gen. Psychiatry* 48, 563-568.

Pettegrew J W, Klunk W E, Kanal E, Panchalingam K and McClure R J (1995) Changes in brain membrane phospholipid and high-energy phosphate metabolism precede dementia. *Neurobiol. Aging* 16, 973-975.

Pettegrew J W, Kopp S J, Dadok J, Minshew N J, Feliksik J M, Glonek T and Cohen M M (1986) Chemical characterization of a prominent phosphomonoester resonance from mammalian brain: $^{31}P$ and $^{1}H$ NMR analysis at 4.7 and 14.1 tesla. *J. Magn. Reson.* 67, 443-450.

Pettegrew J W, Kopp S J, Minshew N J, Glonek T, Feliksik J M, Tow J P and Cohen M M (1987a) $^{31}P$ nuclear magnetic resonance studies of phosphoglyceride metabolism in developing and degenerating brain: Preliminary observations. *J. Neuropathol. Exp. Neurol.* 46, 419-430.

Pettegrew J W, Levine J, Gershon S, Stanley J A, Servan-Schreiber D, Panchalingam K and McClure R J (2002) $^{31}P$-MRS study of acetyl-L-carnitine treatment in geriatric depression: preliminary results. *Bipolar Disorders* 4, 61-66.

Pettegrew J W and Minshew N J (1981) Effects of short chain fatty acids on cellular membranes and energy metabolism: A nuclear magnetic resonance study. *Neurology* 31, 143.

Pettegrew J W, Minshew N J, Glonek T, Kopp S J and Cohen M M (1982a) Phosphorus NMR study of gerbil stroke model. *Neurology* 32, 196.

Pettegrew J W, Minshew N J, Spiker D, McClure R J and Klunk W E (1993a) Membrane alterations in erythrocytes of affective illness patients. *Biol. Psychiatry* 33, 47A.

Pettegrew J W, Minshew N J, Spiker D, Tretta M, Strychor S, McKeag D, Munez L R, Miller G M, Carbone D and McClure R J (1993b) Alterations in membrane molecular dynamics in erythrocytes of patients with affective illness. *Depression* 1, 88-100.

Pettegrew J W, Minshew N J and Stewart R M (1981 a) Dynamic membrane studies in individuals at risk for Huntington's disease. *Neurology* 31, 151.

Pettegrew J W, Moossy J, Withers G, McKeag D and Panchalingam K (1988a) $^{31}P$ Nuclear Magnetic Resonance study of the brain in Alzheimer's disease. *J Neuropathol. Exp. Neurol.* 47, 235-248.

Pettegrew J W, Nichols J S, Minshew N J, Rush A J and Stewart R M (1982b) Membrane biophysical studies of lymphocytes and erythrocytes in manic-depressive illness. *J. Affective Disord.* 4, 237-247.

Pettegrew J W, Nichols J S and Stewart R M (1979b) Fluorescence spectroscopy on Huntington's fibroblasts. *J. Neurochem.* 33, 905-911.

Pettegrew J W, Nichols J S and Stewart R M (1979c) Fluorescence studies of fibroblasts, lymphocytes, and erythrocytes in Huntington's disease. *Ann. Neurol.* 6, 164.

Pettegrew J W, Nichols J S and Stewart R M (1980a) Membrane biophysical studies in manic-depressive intact peripheral tissues. *Neurology* 30, 375.

Pettegrew J W, Nichols J S and Stewart R M (1980b) Membrane studies in Huntington's disease: steady-state fluorescence studies of intact erythrocytes. *Ann. Neurol.* 8, 381-386.

Pettegrew J W, Nichols J S and Stewart R M (1981b) Membrane studies in Huntington's disease: Steady-state and time-dependent fluorescence spectroscopy of intact lymphocytes. *J. Neurochem.* 36, 1966-1976.

Pettegrew J W, Panchalingam K, Hamilton R L and McClure R J (2001) Brain membrane phospholipid alterations in Alzheimer's disease. *Neurochem. Res.* 26, 771-782.

Pettegrew J W, Panchalingam K, Klunk W E, McClure R J and Muenz L R (1994) Alterations of cerebral metabolism in probable Alzheimer's disease: A preliminary study. *Neurobiol. Aging* 15, 117-132.

Pettegrew J W, Panchalingam K, Moossy J, Martinez J, Rao G and Boller F (1988b) Correlation of phosphorus-31 magnetic resonance spectroscopy and morphologic findings in Alzheimer's disease. *Arch. Neurol.* 45, 1093-1096.

Pettegrew J W, Panchalingam K, Spiker D, Minshew N, McKeag D, Strychor S and Tretta M (1998) Membrane molecular dynamics in affective illness. *Soc. Biol. Psychiatry, 43rd Annual Sci. Program* 364.

Pettegrew J W, Panchalingam K, Withers G, McKeag D and Strychor S (1990a) Changes in brain energy and phospholipid metabolism during development and aging in the Fischer 344 rat. *J. Neuropathol. Exp. Neurol.* 49, 237-249.

Pettegrew J W, Short J W, Woessner R D, Strychor S, McKeag D W, Armstrong J, Minshew N J and Rush A J (1987b) The effect of lithium on the membrane molecular dynamics of normal human erythrocytes. *Biol. Psychiatry* 22, 857-871.

Pettegrew J W, Strychor S, Tretta M and McKeag D (1990b) Membrane molecular alterations in Alzheimer's erythrocytes. *Neurology* 40 (Suppl. 1), 404.

Pettegrew J W, Strychor S, Tretta M and McKeag D (1990c) Membrane molecular alterations in Alzheimer's erythrocytes (abstract). *Neurology* 40 (Suppl. 1), 404.

Pettegrew J W, Klunk W E, Panchalingam K, Kanfer J N & McClure R J. Clinical and neurochemical effects of acetyl-L-carnitine in Alzheimer's disease. *Neurobiol Aging* 16:1-4, 1995.

Pettegrew J W, McClure R J, Keshavan M S, Minshew N J, Panchalingam K & Klunk W E. $^{31}P$ magnetic resonance spectroscopy studies of developing brain. In: *Neurodevelopement & Adult Psychopathology*, edited by M S Keshavan & R M Murray. Cambridge University Press, 1997, p. 71-92.

Pettegrew J W, Withers G, Panchalingam K & Post J F. Considerations for brain pH assessment by $^{31}P$ NMR. *Magn Reson Imaging* 6:135-142, 1988.

Pettegrew J W, Levine J, and McClure R J. Acetyl-L-carnitine physical-chemical, metabolic, and therapeutic properties: Relevance for its mode of action in Alzheimer's disease and geriatric depression. *Molecular Psychiatry* 5, 616-632, 2000.

Pfefferbaum A, Lim K O, Rosenbloom M & Zipursky R B. Brain magnetic resonance imaging: Approaches for investigating schizophrenia. *Schizophr Bull* 16:453-476, 1990.

Piovesan P, Pacifici L, Taglialatela G, Ramacci M T & Angelucci L. Acetyl-L-carnitine treatment increases choline acetyltransferase activity and NGF levels in the CNS of adult rats following total fimbria-fornix transection. *Brain Res* 633: 77-82, 1994.

Piovesan P, Quatrini G, Pacifici L, Taglialatela G & Angelucci L. Acetyl-L-carnitine restores choline acetyltransferase activity in the hippocampus of rats with partial unilateral fimbria-fornix transection. *International Journal of developmental Neuroscience* 13:13-19, 1995.

Prickaerts J, Blokland A, Honig W, Meng F & Jolles J. Spatial discrimination learning and choline acetyltransferase activity in streptozotocin-treated rats: effects of chronic treatment with acetyl-L-carnitine. *Brain Res* 674:142-146, 1995.

Provencher S W. Estimation of metabolite concentrations from localized in vivo proton NMR spectra. *Magn Reson Med* 30:672-679, 1993.

Rabins P V, Pearlson G D & Aylward E. Cortical magnetic resonance imaging changes in elderly inpatients with major depression. *Am J Psychiatry* 148:617-620, 1991.

Ramasubbu R (2001) Dose-response relationship of selective serotonin reuptake inhibitors treatment-emergent hypomania in depressive disorders. *Acta Psychiatr. Scand.* 104, 236-238.

Rao K V, Mawal Y R & Qureshi I A. Progressive decrease of cerebral cytochrome C oxidase activity in sparse-fur mice: role of acetyl-L-carnitine in restoring the ammonia-induced cerebral energy depletion. *Neurosci Lett* 224:83-86, 1997.

Rasband W. *NIH Image Manual*. Bethesda, Md.: National Institutes of Health, 1993.

Reynolds C F, Frank E, Kupfer D J, Thase M E, Perel J M, Mazumdar S & Houck P R. Treatment outcome in recurrent major depression: A post-hoc comparison of elderly ("young old") and mid-life patients. *Am J Psychiatry* 153:1288-1292, 1996.

Reynolds C F, Frank E, Perel J, Mazumdar S & Kupfer D J. Maintenance therapies for late-life recurrent major depression: Research and review circa 1995. *International Psychogeriatrics* 7:27-40, 1995.

Reynolds C F, Nowell P D, Hoch C C, Neylan T C, Buysse D J & Kupfer D J. Diagnosis and treatment of insomnia in the elderly. In: *Clinical Geriatric Psychopharmacology*, edited by C Salzman. 1997, Ricci A, Ramacci M T, Ghirardi O & Amenta F. Age-related changes of the mossy fibre system in rat hippocampus: effect of long term acetyl-L-carnitine treatment. *Arch Gerontol Geriatrics* 8:63-71, 1989.

Risch S C, Kalin N H & Janowsky D S. Cholinergic challenges, behavioral and neuroendocrine correlates. *J Clin Psychopharmacol* 1:186-192, 1981.

Rosenberg D R, Keshavan M S, Dick E L, Bagwell W W, McMaster F, Seymour A B & Birmaher A B. Quantitative morphology of the corpus callosum in pediatric obsessive compulsive disorder. *Prog Neuropsychopharmacology Biol Psychiatry*, in press, 1997.

Rosenthal R E, Williams R, Bogaert Y E, Getson P R & Fiskum G. Prevention of postischemic canine neurological injury through potentiation of brain energy metabolism by acetyl-L-carnitine. *Stroke* 23:1312-1318, 1992.

Rovner B W. Depression and increased risk of mortality in the nursing home patient. *Am J Med* 94:19S-22S, 1993.

Ruggiero F M, Cafagna F, Gadaleta M N & Quagliariello E. Effect of aging and acetyl-L-carnitine on the lipid composition of rat plasma and erythrocytes. *Biochem Biophys Res Commun* 170:621-626, 1990.

Sachs G S, Printz D J, Kahn D A, Carpenter D, & Docherty J P. The Expert Consensus Guideline Series: Medication Treatment of Bipolar Disorder, *Postgraduate Med.* April, Spec:1-104, 2000.

Sass R L & Wemess P. Acetylcarnitine on the relationship between structure and function. *Biochem Biophys Res Commun* 55:736-742, 1973.

Schlegel S, Aldenhoff J B, Eissner D, Linder P & Nickel O. Regional cerebral blood flow in depression: Associations with psychopathology. *J Affective Disord* 17:211-218, 1989.

Seelig J. 31P nuclear magnetic resonance and the head group structure of phospholipids in membranes. *Biochim Biophys Acta* 515:105-140, 1978.

Sershen H, Harsing L J, Banay-Schwartz M, Hashim A, Ramacci M T & Lajtha A. Effect of acetyl-L-carnitine on the dopaminergic system in aging brain. *J Neurosci Res* 30:555-559, 1991.

Singh I, Xu C, Pettegrew J W and Kanfer J N (1994) Endogenous inhibitors of human choline acetyltransferase present in Alzheimer's brain: Preliminary observation. *Neurobiol. Aging* 15, 643-649.

Smith I C P & Ekiel I H. Phosphorus-31 NMR of Phospholipids in Membranes. In: *Phosphorus-31 NMR: Principles and Applications*, Academic Press, 1984, p. 447-474.

Stanley J A, Drost D J, Williamson P C & Thompson R T. The use of a priori knowledge to quantify short echo in vivo $^1$H MR spectra. *Magn Reson Med* 34:17-24, 1995.

Stanley J A, Panchalingam K, Miller G, McClure R J & Pettegrew J W. A new method to quantify the broad component under the phosphodiester resonance and its application to study first-episode never medicated schizophrenics [abstract]. *Proceedings of the 5th Annual meeting of the International Society of Magnetic Resonance in Medicine* SMR, Berkeley Calif.: 1408, 1997.

Stanley J A, Williamson P C, Drost D J, Carr T, Tylett J & Merskey H. The study of schizophrenia via in vivo $^{31}$P and $^1$H MRS. *Schizophr Bull* 9:210-210, 1993.

Stanley J A, Williamson P C, Drost D J, Carr T J, Rylett R J, Morrison-Stewart S & Thompson R T. Membrane phospholipid metabolism and schizophrenia: An in vivo $^{31}$P-MR spectroscopy study. *Schizophr Res* 13:209-215, 1994.

Stanley M & Mann J J. Increased serotonin: 2-binding sites in frontal cortex of suicide victims. *Lancet* i:214-216, 1983.

Stark P & Hardison C D. A review of multicentre controlled studies of fluoxetine vs imipramine and placebo in our patients with major depressive disorder. *J Clin Psychiatry* 46:26-31, 1985.

Stevens M J, Lattimer S A, Feldman E L, Helton E D, Millington D S, Sima A A & Greene D A. Acetyl-L-carnitine deficiency as a cause of altered nerve myo-inositol content, Na,K-ATPase activity, and motor conduction velocity in the streptozotocin-diabetic rat. *Metabolism: Clinical & Experimental* 45:865-872, 1996.

Sweet R A, Panchalingam K, Pettegrew J W, McClure R J, Hamilton R L, Lopez O L, Kaufer D I, DeKosky S T and Klunk W E (2002) Psychosis in Alzheimer disease: postmortem magnetic resonance spectroscopy evidence of excess neuronal and membrane phospholipid pathology. *Neurobiol. Aging* 23, 547-553.

Szanto K, Prigerson H G, Houck P R & Reynolds C F. Suicidal ideation in elderly bereaved: The role of complicated grief. *Suicide and Life-Threatening Behavior* 27:194-207, 1997.

Taglialatela G, Angelucci L, Ramacci M T, Werrbach-Perez K, Jackson G R & Perez-Polo J R. Acetyl-L-carnitine enhances the response of PC12 cells to nerve growth factor. *Brain Res Develop Brain Res* 59:221-230, 1991.

Taglialatela G, Angelucci L, Ramacci M T, Werrbach-Perez K, Jackson G R & Perez-Polo J R. Stimulation of nerve growth factor receptors in PC12 by acetyl-L-carnitine. *Biochem Pharmacol* 44:577-585, 1992.

Taglialatela G, Navarra D, Cruciani R, Ramacci M T, Alema G S & Angrist B. Acetyl-L-carnitine treatment increases nerve growth factor levels and choline acetyltransferase activity in the central nervous system of aged rats. *Exp Gerontol* 29:55-66, 1994.

Talairach J & Toumoux P. *Co-planar Stereotaxic Atlas of the Human Brain*. New York: Thieme Medical Publishers, 1988.

Tamada R S, Issler C K, Amaral J A, Sachs G S and Lafer B (2004) Treatment emergent affective switch: a controlled study. *Bipolar Disorders* 6, 333-337.

Tempesta E, Casella L, Pirrongelli C, Janiri L, Calvani M & Ancona L. L-acetlycarnitine in depressed elderly subjects. A cross-over study vs placebo. *Drugs Under Experimental Clin Res* 13:417-423, 1987.

Tempesta E, Janiri L & Pirrongelli C. Stereospecific effects of acetylcarnitine on the spontaneous activity of brain-stem neurons and their responses to acetylcholine and serotonin. *Neuropharmacology* 24:43-50, 1985.

Tempesta E, Janiri L & Salera P. The effects of microiontophoretically applied acetyl-L-carnitine on single neurons in the rats brain-stem. *Neuropharmacology* 21:111982.

Traskman L, Asberg M, Bertilsson L & Sjostrand L. Monoamine metabolites in CSF and suicidal behavior. *Arch Gen Psychiatry* 38:631-636, 1981.

Urenjak J, Williams S R, Gadian D G & Noble M. Specific expression of N-acetylaspartate in neurons, oligodendrocyte-type-2 astrocyte progenitors, and immature oligodendrocytes in vitro. *J Neurochem* 59:55-61, 1992.

van der Veen J W, de Beer R, Luyten P R & van Ormondt D. Accurate quantification of in vivo $^{31}$P NMR signals using the variable projection method and prior knowledge. *Magn Reson Med* 6:92-98, 1988.

Vance D E. Phospholipid metabolism and cell signalling in eucaryotes. In: *Biochemistry of lipids, lipoproteins and membranes, Volume* 20, edited by D E Vance & J Vance. New York: Elsevier, 1991, p. 205-240.

Villa R F & Gorini A. Action of L-acetylcarnitine on different cerebral mitochondrial populations from hippocampus and striatum during aging. *Neurochem Res* 16:1125-1132, 1991.

Villa R F, Turpeenoja L, Benzi G & Giuffrida S M. Action of L-acetylcarnitine on age-dependent modifications of mitochondrial membrane proteins from rat cerebellum. *Neurochem Res* 13:909-916, 1988.

Villardita C, Smirni P & Vecchio I. Acetyl-L-carnitine in depressed geriatric patients. *Eur Rev Med Pharm Sci* 6:1-12, 1983.

Wee B E & Turek F W. Carbachol phase shifts the circadian rhythm of locomotor activity in the jungarian hamster. *Brain Res* 505:209-214, 1989.

Most of the studies have been directed toward geriatric subjects. However, it is also desirable to use acetyl-L-carnitine (ALCAR) for non-geriatric human subjects as well as for adolescent human subjects.

SUMMARY OF THE INVENTION

In accordance with preferred embodiments of the present invention, some of the problems presently associated with the diagnosis of alcoholism disease are overcome. A method and system for medical imaging of neuropsychiatric disorders including chronic alcoholism is presented.

The method allows cognitive impairment seen in some chronic alcoholism subjects to be determined. Regional molecular/metabolic alterations of phospholipid and ganglioside metabolism are determined which distinguish cognitively impaired and cognitively unimpaired chronic alcoholism subjects.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 3A is a phosphorous magnetic resonance spectroscopic image showing the Z-scores of the two depressed subjects compared with controls at entry and 12 weeks for PME(s-$\tau_c$) metabolite levels for those regions with significant differences. The intensity of the color is scaled to the z-score (mean difference/SD) given on the scale below the image. Z-scores for PME(s-$\tau_c$) and PCr levels in the frontal region exceed 3.0 and 2.0, respectively;

FIG. 3B is a phosphorous magnetic resonance spectroscopic image showing the Z-scores of the two depressed subjects compared with controls at entry and 12 weeks for PCr metabolite levels for those regions with significant differences. The intensity of the color is scaled to the z-score (mean difference/SD) given on the scale below the image. Z-scores for PME(s-$\tau_c$) and PCr levels in the frontal region exceed 2.0 and 2.0, respectively;

Figure 7:
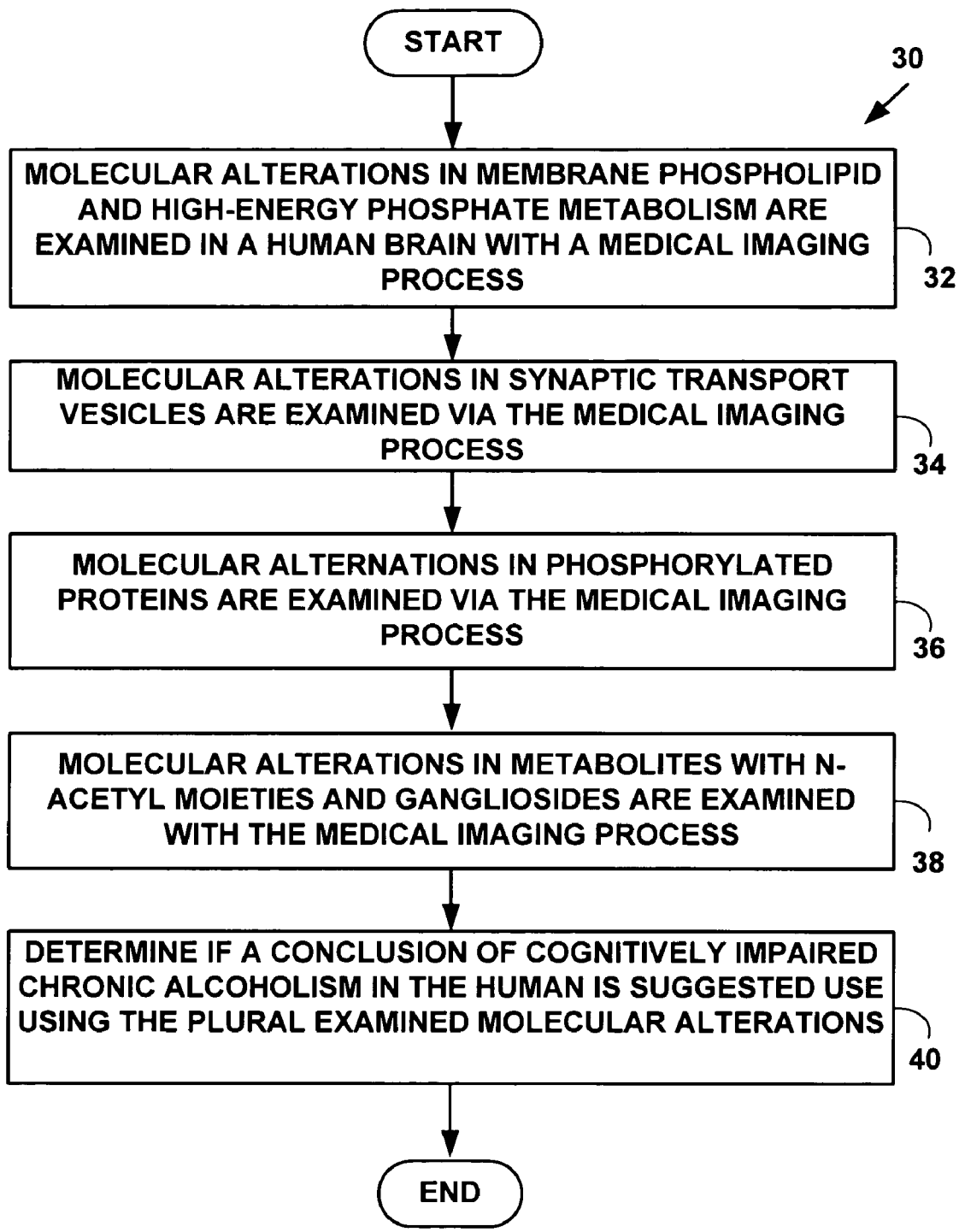
Figure 8:
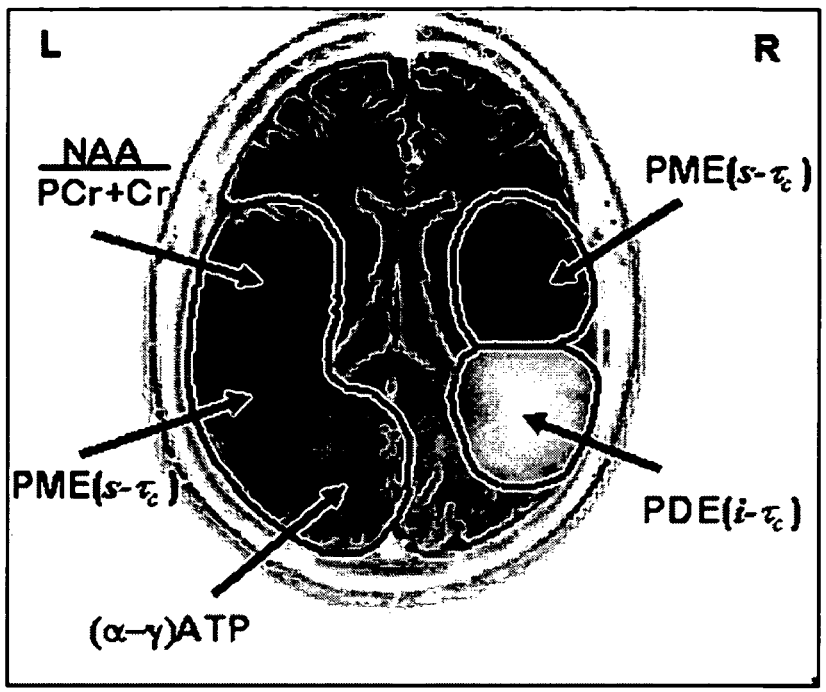
Figure 9:
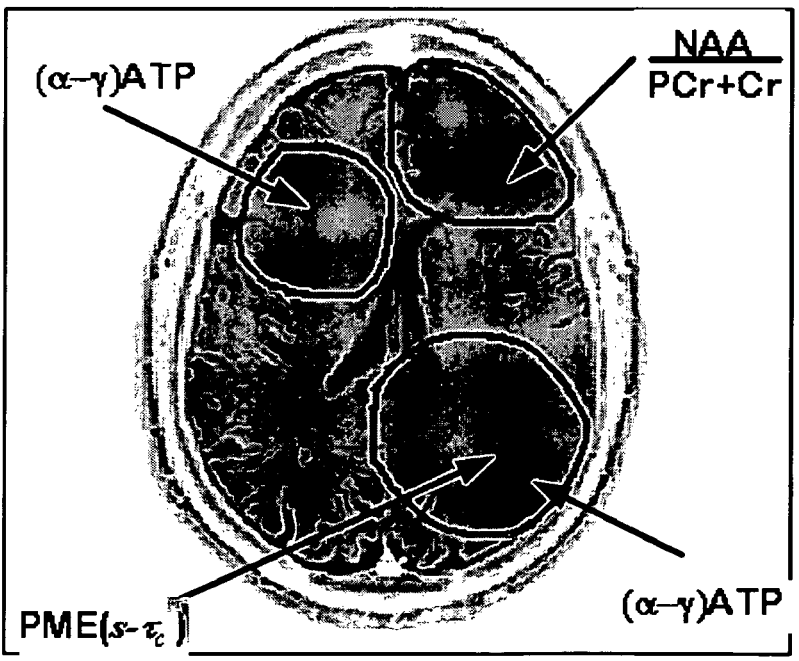
Figure 10:
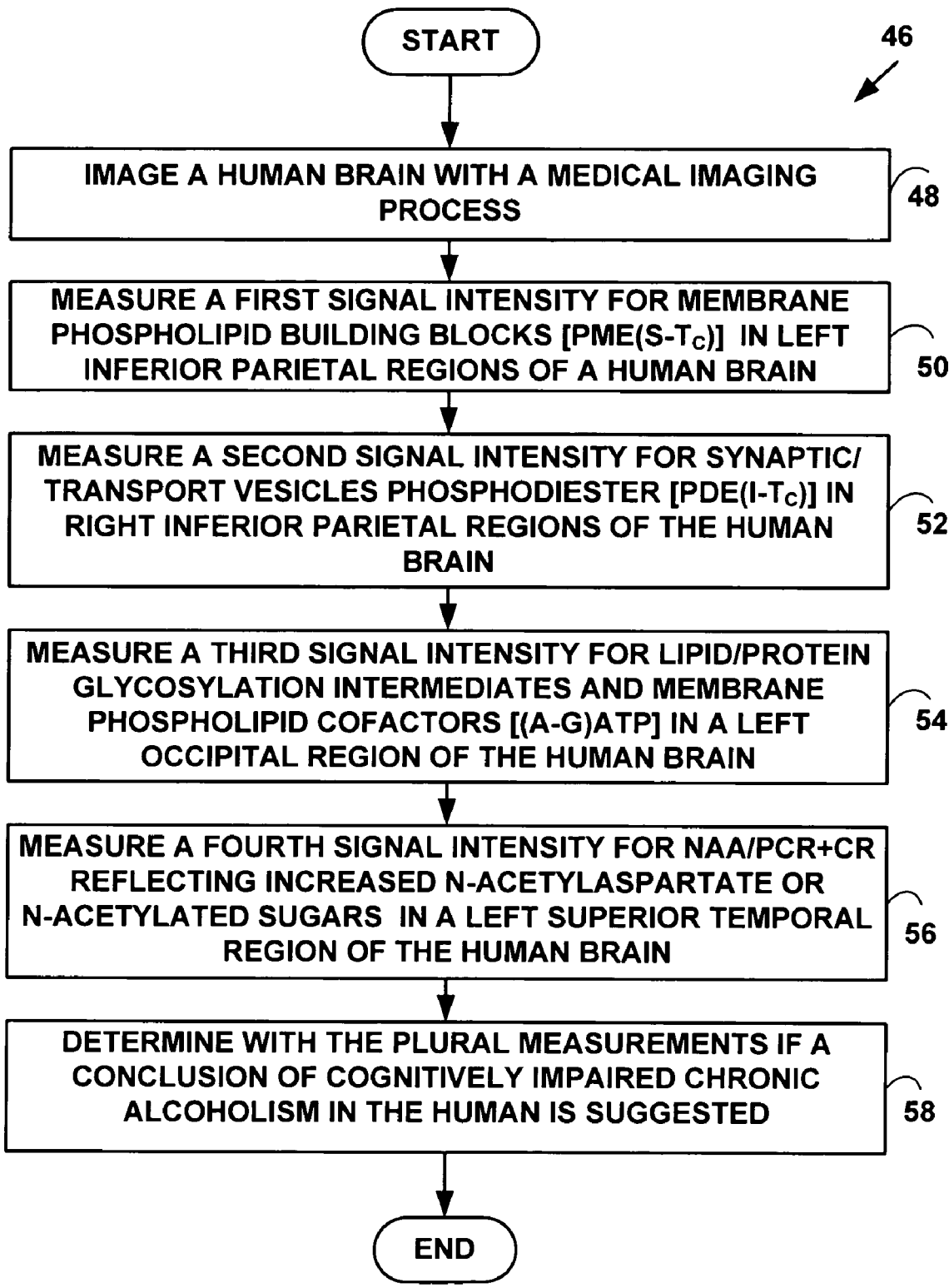
Figure 11:
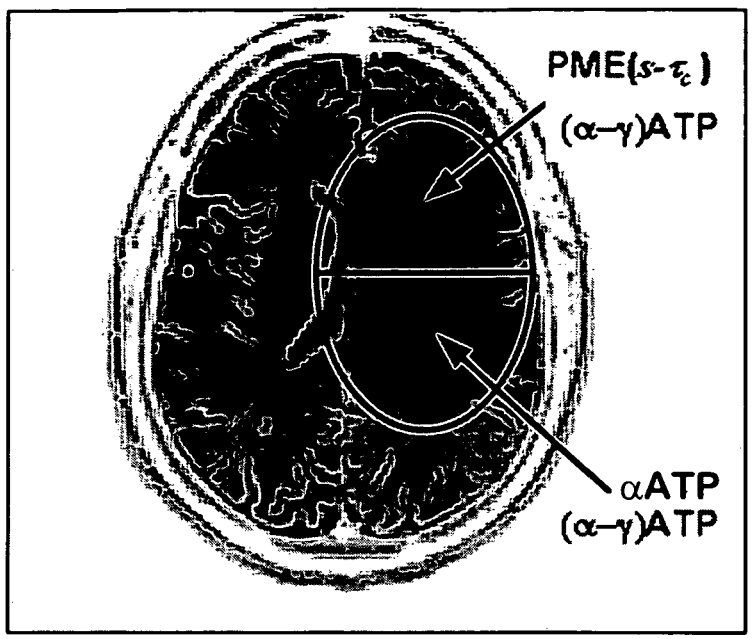
Figure 12:
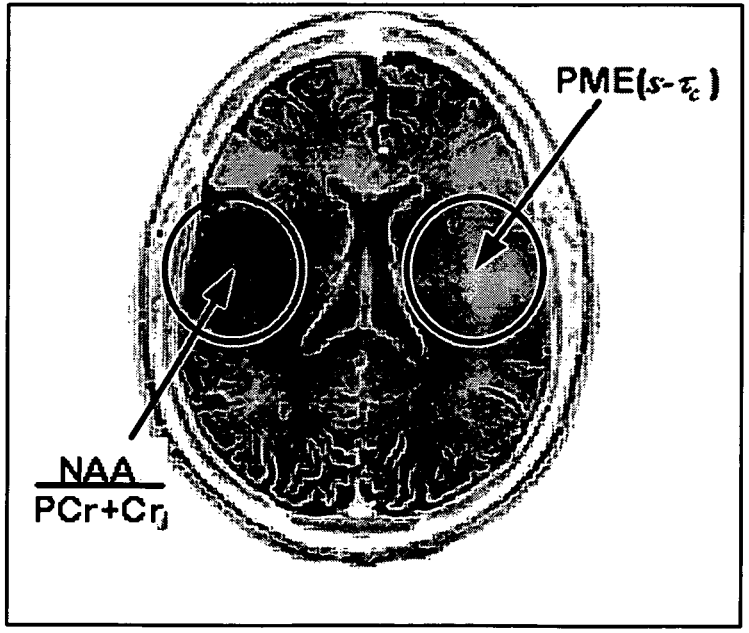
Figure 13:
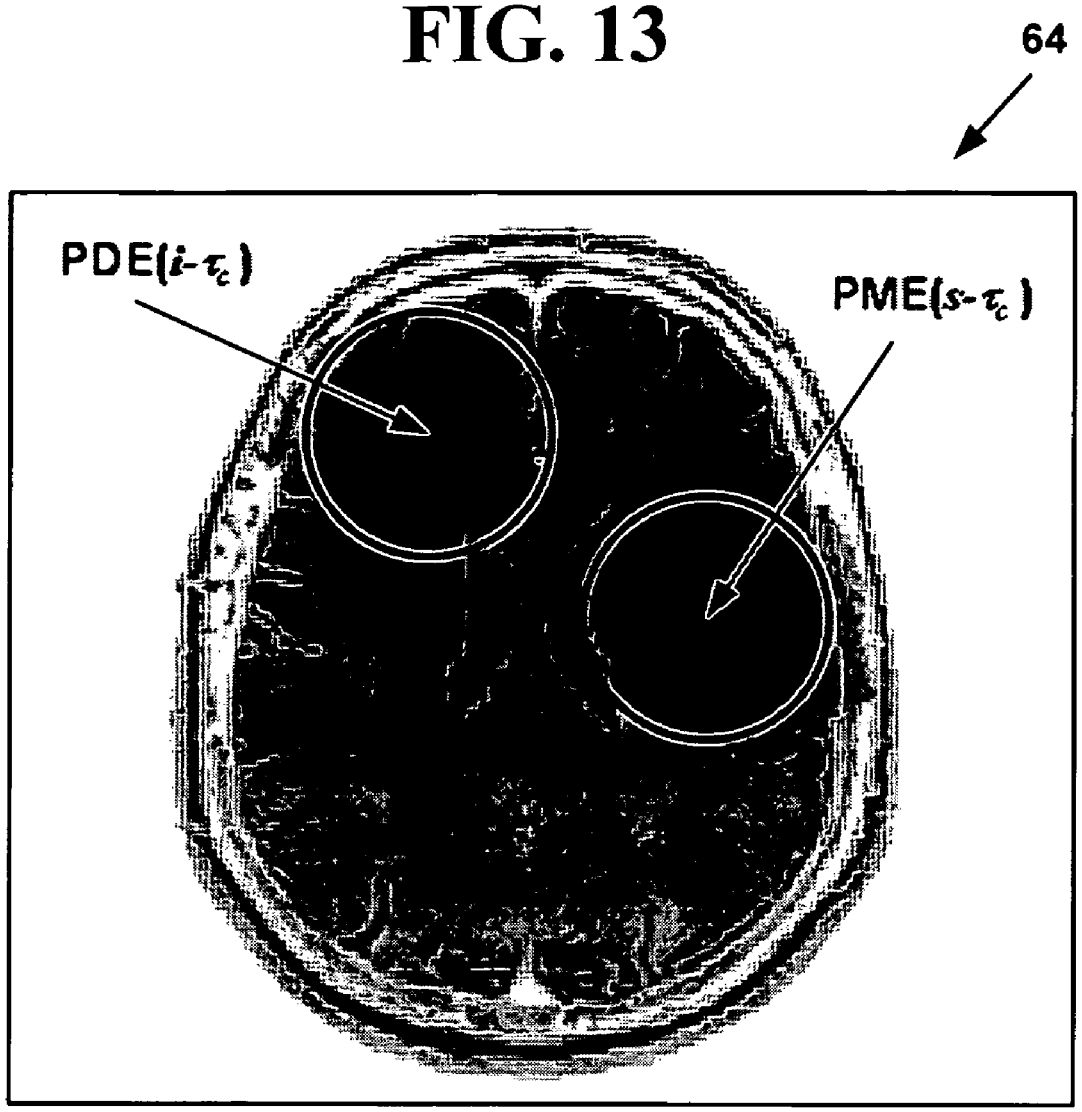

[full width at half maximum (fwhm)] of 2 MDD subjects compared with 13 control subjects;

FIG. 7 is a flow diagram illustrating a method for diagnosing chronic alcoholism in a human;

FIG. 8 is a block diagram of a phosphorous magnetic resonance spectroscopic image illustrating Chronic Alcoholism in Males Cognitively Impaired (N=4) vs Cognitively Unimpaired (N=5);

FIG. 9 is a block diagram of a phosphorous magnetic resonance spectroscopic image illustrating Correlations—MRS metabolites versus Neuropsychological Scores (N=9);

FIG. 10 is flow diagram illustrating a Method 46 for diagnosing chronic alcoholism in a human;

FIG. 11 is a block diagram of a phosphorous magnetic resonance spectroscopic image illustrating Chronic Schizophrenia (males): Cognitively Impaired (N=19) vs Cognitively Unimpaired (N=16);

FIG. 12 is a block diagram of a phosphorous magnetic resonance spectroscopic image illustrating Correlations—MRS Metabolites vs. Neuropsychological Scores (N=35); and FIG. 13 is a block diagram 64 of a phosphorous magnetic resonance spectroscopic image illustrating Effects of Nicotine: Middle Age Smokers (N=8), Nicotine vs. Placebo Patch.

DETAILED DESCRIPTION OF THE INVENTION

Carnitines in general are compounds of including the chemical formula (1):

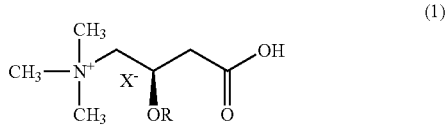

(1)

where R is hydrogen or an alkanoyl group with 2 to 8 carbon atoms, and $X^-$ represents the anion of a pharmaceutically acceptable salt.

The invention described herein includes both the administration of L-carnitine or an alkanoyl L-carnitine or one of its pharmacologically acceptable salts of formula (1) in the treatment of depression, and pharmaceutical compositions, which can be administered orally, parenterally or nasally, including controlled-release forms. Preferably, the alkanoyl L-carnitine is selected from the group consisting of acetyl-L-carnitine (hereinafter abbreviated to ALC or ALCAR), propionyl L-carnitine (hereinafter abbreviated to PLC), butyryl L-carnitine, valeryl L-carnitine and isovaleryl L-carnitine, or one of their pharmacologically acceptable salts. The ones preferred are acetyl L-carnitine, propionyl L-carnitine and butyryl L-carnitine. The most preferred is acetyl L-carnitine.

What is meant by a pharmacologically acceptable salt alkanoyl L-carnitine is any salt of the latter with an acid that does not give rise to toxic or side effects. These acids are well known to pharmacologists and to experts in pharmaceutical technology.

Examples of pharmacologically acceptable salts of L-carnitine or of the alkanoyl L-carnitines, though not exclusively these, are chloride; bromide; iodide; aspartate; acid aspartate; citrate; acid citrate; tartrate; acid tartrate; phosphate; acid phosphate; fumarate; acid fumarate; glycerophosphate; glucose phosphate; lactate; maleate; acid maleate; mucate; orotate, oxalate; acid oxalate; sulphate; acid sulphate; trichloroacetate; trifluoroacetate; methane sulphonate; pamoate and acid pamoate.

As used herein, a geriatric subject is an individual sixty-five years of age or older. See The Merck Manual, 15th edition (1987) p. 2389. A non-geriatric subject is less than sixty-five years old but not an adolescent.

Adolescence is the transitional stage of development between childhood and full adulthood, representing the period of time during which a person is biologically adult but emotionally may not at full maturity. The ages which are considered to be part of adolescence vary by culture. In the United States, adolescence is generally considered to begin around age thirteen, and end around twenty-four. By contrast, the World Health Organization (WHO) defines adolescence as the period of life between around age ten and end around age twenty years of age. As used herein, an adolescent subject is at least ten years old and less than twenty-six years old.

Phosphorus magnetic resonance spectroscopic imaging ($^{31}$P MRSI) analysis of two depressed elderly subjects treated with ALCAR for 12 weeks are compared with those of six normal non-demented, non-depressed subjects.

A twelve-week, open, clinical, $^{31}$P MRSI study design was used to examine the possible effects of ALCAR on brain metabolism and depressive symptomatology in non-demented geriatric major depressive disorder (NDG-MDD). Two depressed, non-demented [Folstein Mini-Mental State Exam (MMSE)>24)] male subjects, 70 and 80 years old, were compared with six age, social-economic status, and medically matched non-demented controls (all male, mean age of 73.6±3.6 years, range 69.7-78.2 years). The two elderly depressed subjects completed baseline Structural Clinical Interview of DSM-IV (SCID) I/P version 2.0, HDRS (17 item), MMSE, UKU Side Effect Rating Scale (UKU), and Cumulative Illness Rating Scale (CIRS) to assess medical burden, baseline physical, ECG, and, laboratory tests for hematology, urine analysis, immunopathology, and blood chemistry. Follow-up visits for the depressed subjects were done every other week for 12 weeks. Efficacy (psychiatric evaluation) was assessed by changes in the HDRS which was performed at baseline and every other week for 12 weeks along with secondary measures (MMSE; CIRS; and UKU), whereas the CIRS was performed at baseline, 6, and 12 weeks. Physical examinations and EKGs were performed at baseline, 6, and 12 weeks. The baseline MR evaluation was scheduled and completed prior to the administration of ALCAR. Follow-up MR evaluations were at 6 and 12 weeks. Acetyl-L-carnitine was administered in the form of oral tablets containing 590 mg of acetyl-L-carnitine hydrochloride (500 mg acetyl-L-carnitine). The dosage regimen was fixed at three grams of acetyl-L-carnitine given two tablets three times a day for 12 weeks.

$^{31}$P MRSI acquisition—A custom built, doubly tuned transmit/receive volume head coil was used to acquire the $^1$H MRI and 2D $^{31}$P MRSI data on a GE Signa 1.5 T whole body MR imager. First, sets of axial and sagittal scout MR images were collected. The 30 mm thick MRSI slice was positioned parallel with the anterior commisure-posterior commisure line to include the right and left prefrontal, basal ganglia, superior temporal, inferior parietal, occipital, and centrum semiovale regions. A self-refocused spin echo pulse sequence with an effective flip range of 60° and an echo time of 2.5 ms, was used to acquire the $^{31}$P MRSI (360 mm field of view, 30 mm slice thickness, 8×8 phase encoding steps [45×45×30 mm$^3$ nominal voxel dimensions],2 s TR, 1024 data points, 4.0 kHz spectral bandwidth and 16 NEX).

MRSI post-processing and quantification—To optimize the right and left voxel positions for the six regions, the 8×8 $^{31}$P grid was shifted with respect to the anatomical MRI and a mild spatial apodization (i.e., Fermi window with 90% diameter and 5% transition width) was applied prior to the inverse Fourier transform. The remaining processing steps were 100% automated. A 5 Hz exponential apodization was applied and the PME, phosphodiester (PDE), PCr, α-, γ-, and β-ATP, and inorganic orthophosphate (Pi), were modeled in the time domain with exponentially damped sinusoids and by omitting the first 2.75 ms of the free induction decay (FID) using the Marquardt-Levenberg algorithm. This approach ensured that the PME and PDE resonances primarily reflected the freely mobile, short correlation time (s-$\tau_c$), water soluble PME(s-$\tau_c$) and PDE(s-$\tau_c$) metabolites without the influence of relatively broad underlying signals within the PME and PDE spectral region. The PME(s-$\tau_c$) (i.e., phosphoethanolamine, phosphocholine, and inositol-1-phosphate) are predominantly building blocks of phospholipids and therefore, the relative concentrations of these metabolites are a measure of the active synthesis of membranes; the PDE(s-$\tau_c$) (i.e., glycerophosphocholine and glycerophosphoethanolamine) are major products of membrane degradation. To obtain intermediate correlation time (i-$\tau_c$) components within the PME and PDE spectral region, the FIDs were modeled a second time but with omitting the first 0.75 ms of the FID and then taking the difference between the PME and PDE amplitudes of the two modeled results. PME(i-$\tau_c$) moieties include less mobile molecules such as phosphorylated proteins and PMEs that are tightly coupled (in terms of MRS) to macromolecules [i.e., PMEs inserting into membrane phospholipids. PDE(i-$\tau_c$) moieties include less mobile PDEs that are part of small membrane phospholipid structures such as micelles, synaptic vesicles, and transport/secretory vesicles and PDE moieties coupled to larger molecular structures (i.e., PDEs inserting into membrane phospholipid structures. The right/left side effect was eliminated by averaging the signal from the two voxels, prior to fitting (which included correcting for phase and resonance frequency). Additionally, metabolite levels are expressed as a mole % relative to the total $^{31}$P signal.

The statistical analysis was done using the Statview (SAS Institute, Inc.) software package. The pearson t correlation test used to correlate between variables.

The two elderly depressed subjects were diagnosed with MDD according to DSM-IV criteria. No previous antidepressant medications were taken by the subjects in the three months prior to the study. Subject #1 has baseline, 6 and 12 week HDRS scores of 15, 1 and 0 and subject #2 had scores of 20, 17, and 3, respectively. Thus both depressed subjects were clinically improved at endpoint, fulfilling criteria for remission (HDRS<8). Medical conditions diagnosed in the depressed subjects included s/p knee arthroscopy, s/p cervical disk removal, hearing loss and benign prostatic hypertrophy in subject #1 and benign prostatic hypertrophy in subject #2. No clinically significant abnormalities were found in the laboratory exams and EKG of either depressed subject. Baseline, 6, and 12 weeks CIRS were 7, 6, and 5 for subject #1; and 4, 4, and 2 for subject #2, respectively. The change reflects the improvement of depressive symptomatology. Side effects from ALCAR treatment were mild and included dry mouth in subject #1 and a slight increase in perspiration in subject #2.

Figure 1A:
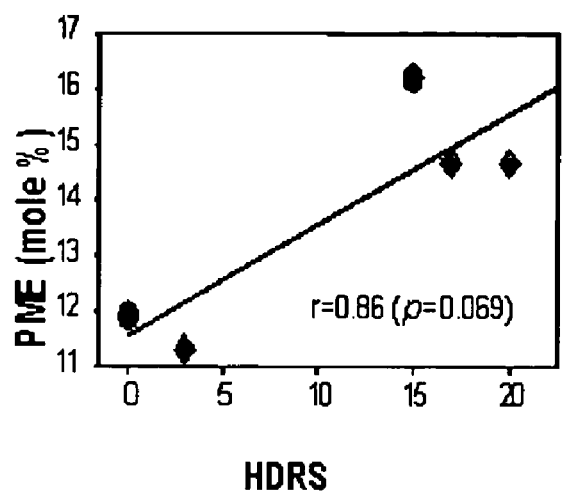
FIG. 1A is a graph showing the correlation of PME(s-$\tau_c$) levels from the prefrontal region with HDRS scores for both depressed patients (● subject #1; ♦ subject #2)
Figure 1B:
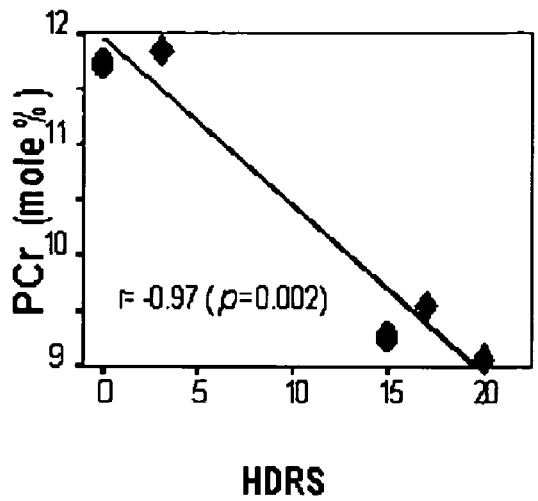
FIG. 1B is a graph showing the correlation of PCr levels from the prefrontal region with HDRS scores for both depressed patients (● subject #1; ♦ subject #2)
Figure 2A:
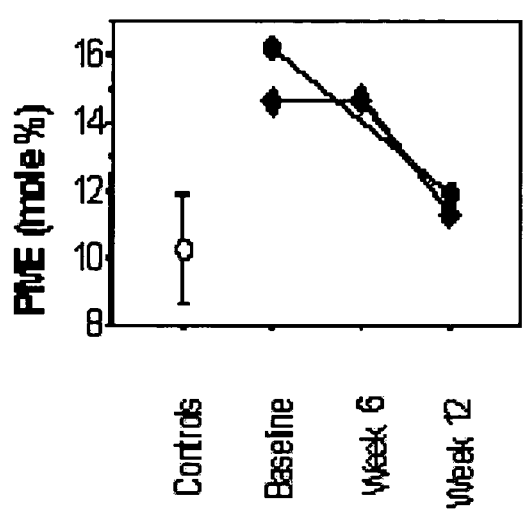
FIG. 2A and FIG. 2B are graphs showing PME(s-$\tau_c$) and PCr levels in the prefrontal region of the two depressed patients (● subject #1; ♦ subject #2) and normal controls (O, n=6) at baseline and at 6 and 12 weeks follow up. The control values include mean±SD.
Figure 2B:
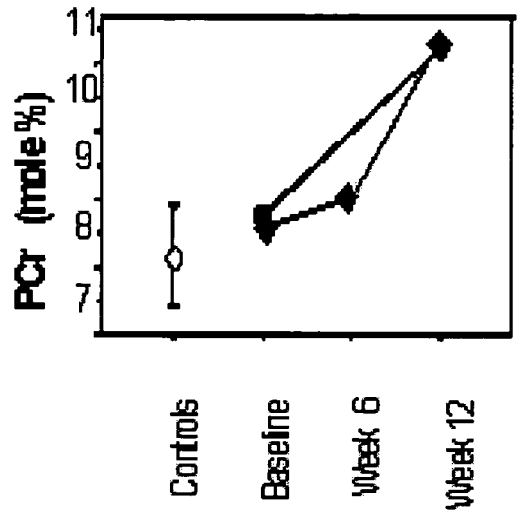
Figure 2C:
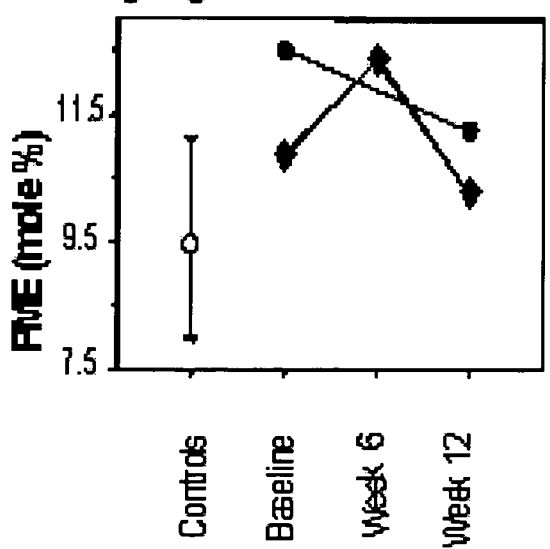
FIG. 2C and FIG. 2D are graphs showing PME(s-$\tau_c$) and PCr levels in the basal ganglia region of the two depressed patients (● subject #1; ♦ subject #2) and normal controls (O, n=6) at baseline and at 6 and 12 weeks follow up. The control values include mean±SD.
Figure 2D:
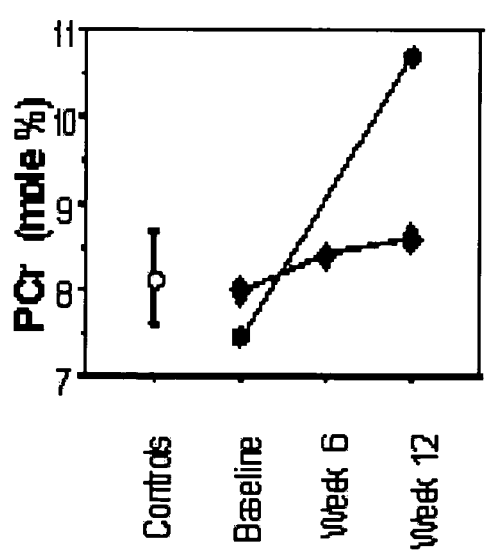

FIG. 1 shows the correlation of PME(s-$\tau_c$) (r=0.86, p=0.069 and PCr (r=0.97, p=0.002) levels from the prefrontal region with HDRS scores for both depressed subjects.

FIG. 2 illustrates the prefrontal and basal ganglia PCr and PME(s-$\tau_c$) levels at baseline, 6 and 12 weeks for the two depressed subjects and the mean PCr and PME(s-$\tau_c$) levels for the six normal controls.

Unfortunately, the 6 week $^{31}$P MRSI session for subject #1 produced poor quality, unacceptable data and this time point is missing from the graphs. Baseline prefrontal PME(s-$\tau_c$) levels in the depressed subjects were 1.5 to 2.0 SD higher than the mean of the controls and this increase was normalized with ALCAR treatment. Both depressed subjects had prefrontal PCr levels one SD higher than the mean of controls and ALCAR treatment further increased PCr levels by 27% and 31%, respectively. Similar changes in PME(s-$\tau_c$) and PCr levels also were observed in the basal ganglia region (FIG. 2), but these metabolite levels did not correlate with HDRS scores. Although the most marked changes occur in the prefrontal region, z-score plots of the significant PME(s-$\tau_c$) and PCr changes between depressed subjects and controls illustrates the other brain regions also undergo changes with ALCAR treatment. FIG. 3 demonstrates that compared with normal subjects, the two untreated depressed subjects at baseline had increased levels of PME(s-$\tau_c$) in the prefrontal region (p=0.006). After 12 weeks of ALCAR treatment, the PME(s-$\tau_c$) are normalized in the prefrontal regions but elevated in the superior temporal regions (p=0.05. In addition, PCr levels are elevated in the prefrontal (p=0.001), basal ganglia (p=0.022), and occipital (p=0.027 regions after 12 weeks of ALCAR treatment. There were no significant changes in the other metabolite levels.

While not wishing to be bound by any particular theory, the above findings suggest that beneficial clinical effects of acetyl-L-carnitine appear to be associated with changes in brain prefrontal PME(s-$\tau_c$) and PCr levels. In the prefrontal region, the depressed subjects compared with controls after 12 weeks of ALCAR treatment show normalization of PME (s-$\tau_c$) and elevation of PCr levels.

The PME(s-$\tau_c$) resonance is predominantly composed of phosphocholine, phosphoethanolamine and inositol-1-phosphate which are precursors in membrane phospholipid metabolism. The increased PME(s-$\tau_c$) in depression, as also observed by others is not fully understood and will require further study. ALCAR treatment seems to restore PME(s-$\tau_c$) levels to normal and there was a trend for the decreasing PME levels to correlate with clinical improvement. In the prefrontal region, twelve weeks of ALCAR treatment also elevated PCr, a high-energy phosphate metabolite which is an immediate precursor of ATP.

Compared with the control group, similar findings were observed for basal ganglia PME(s-$\tau_c$) and PCr levels, but the metabolite levels did not correlate with HDRS scores. This may be due to the small number of depressed patients analyzed. Other brain regions may be affected by depression and these changes may be altered by ALCAR treatment (FIG. 3).

Acetyl-L-Carnitine (ALCAR) Results

MDD is a major, world-wide health problem. There is a need for new treatment approaches that have a wide margin of safety and can speed the onset to remission and reduce the rate of recurrence in this major mental health problem. In addition, the molecular and metabolic factors that underlie MDD and contribute to the slow and variable treatment response are further identified. Since ALCAR has demonstrated beneficial effects on neurodegenerative processes as well as beneficial effects on energy metabolism, membrane structure/function/metabolism, and neurotrophic effects, it is used in treatement of MDD. Many of the metabolic and molecular processes in adolescent and non-geriatric subjects are altered by ALCAR and thus are amenable to ALCAR treatment.

ALCAR treatment decreases levels of phosphomonoesters (PME) and increases levels of phospocreatine (PCr) in a brain of an adolescent or non-geriatric human subject with depression or bi-polar depression. ALCAR also produces beneficial changes to membrane phospholipid and high-energy phosphate metabolism in a brain a brain of an adolescent or non-geriatric human subject with depression or bi-polar depression.

What is meant by a pharmacologically acceptable salt of ALCAR is any salt of the latter with an acid that does not give rise to toxic or side effects. These acids are well known to pharmacologists and to experts in pharmaceutical technology.

One preferred form of daily dosing of ALCAR for clinical use is a composition comprising an amount of an acetyl L-carnitine, preferably equivalent to 0.1 to 3 g, and preferably 0.5 to 3 g per day.

ALCAR does not appear to induce mania in animal models or in clinical trials to date. Since animal and basic science studies demonstrate that ALCAR shares several important molecular mechanisms with lithium, but without lithium's potential toxicity, ALCAR could provide prophylactic effects against suicidality. Given ALCAR's similarity to lithium at several molecular mechanistic levels, ALCAR is effective in treating bipolar depression and preventing recurrent episodes. Long-term therapy of MDD with therapeutic agents that have molecular properties that slow or reverse neurodegenerative changes as well as behavioral changes is desirable. ALCAR is one such therapeutic agent. Few existing $^{31}$P and $^{1}$H MRSI studies of MDD provide findings for compounds which demonstrate both membrane phospholipid and high-energy phosphate changes in the brain of individuals with MDD. However, new studies with ALCAR demonstrate such changes (see below). Since ALCAR can interact with both cholinergic and serotonergic neurotransmitter systems, it will modulate neurobiological and psychobiological activities controlled by these two neurotransmitter systems. This partially explains ALCAR's antidepressant activity.

Effect of ALCAR on Brain Metabolic Response to Brief Energetic Stress

ALCAR has been shown to provide a protective effect in several animal models of brain energetic stress. ALCAR also has been shown to be an effective treatment of MDD which is associated with neurodegenerative and metabolic changes consistent with energetic stress.

Figure 4:
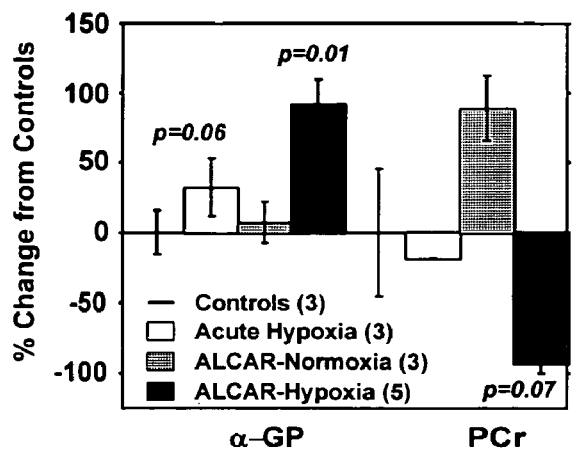
FIG. 4 is a block diagram illustrating an effect of ALCAR on in vitro $^{31}$P MRS α-GP and PCr levels under hypoxic (30 seconds) and normoxic conditions in Fischer 344 rats.

FIG. 4 is a block diagram illustrating an effect of ALCAR on in vitro $^{31}$P MRS α-GP and PCr levels under hypoxic (30 seconds) and normoxic conditions in Fischer 344 rats.

Figure 5:
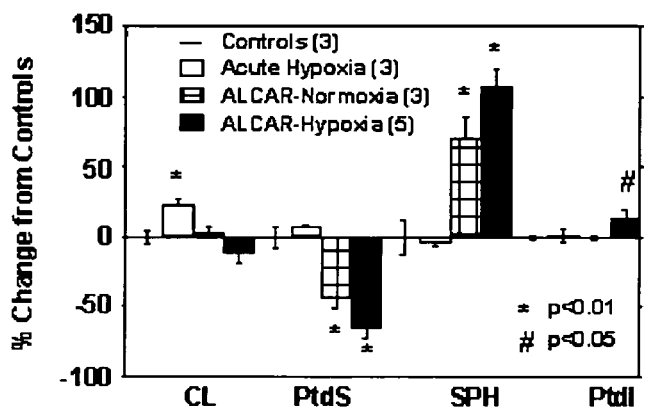
FIG. 5 is a block diagram illustrating an effect of ALCAR on in vitro $^{31}$P MRS phospholipid levels under hypoxic and normoxic conditions in Fischer 344 rats.

FIG. 5 is a block diagram illustrating an effect of ALCAR on in vitro $^{31}$P MRS phospholipid levels under hypoxic and normoxic conditions in Fischer 344 rats.

The rat brain responds differentially to brief energetic stress (30 seconds of hypoxia) depending on the age of the animal. The effect of ALCAR (75 mg/kg animal weight injected intraperitoneally 1 hour before sacrificing the animal) on both normoxic rat brain and rat brain exposed to brief hypoxia (30 seconds) was investigated (FIGS. x and x). These studies were conducted on aged rats (30 months) to provide possible insights into human aged brain and MDD. While ALCAR under normoxic conditions (ALCAR/normoxia) did not alter α-GP levels, under ALCAR/hypoxia conditions, the α-GP levels were elevated higher (approximately +80% compared with controls, p=0.01) than under 30 seconds of hypoxia alone (approximately +25% compared with controls, p=0.06). Mirror-image findings were observed for PCr levels which decrease with hypoxia (non-significant), increase with ALCAR/normoxia (non-significant), and decrease with ALCAR/hypoxia (non-significant, p=0.07)(FIG. 4).

The findings for brain phospholipids are particularly striking (FIG. 5) given the brevity of the hypoxia. Cardiolipin levels are increased (approx. +20%) after 30 seconds of hypoxia (p<0.01), are unchanged with ALCAR/normoxia, and non-significantly reduced with ALCAR/hypoxia. Phosphatidylserine (PtdS) levels are unchanged with hypoxia but are decreased with both ALCAR/normoxia (approx. −50%, p<0.01) and ALCAR/hypoxic (approx. −75%, p<0.01).

These studies provide direct evidence for ALCAR effects on brain membrane phospholipid metabolism and the NADH/α-GP shuttle pathway under conditions of normoxia (PtdS, SPH) and brief hypoxia (α-GP, PtdS, SPH, PtdI). These mechanisms are also important in human clinical conditions that involve brain aging and possible energetic stress such as MDD.

In Vivo $^{31}$P MRS Findings in Two Young Subjects with MDD

Figure 6:
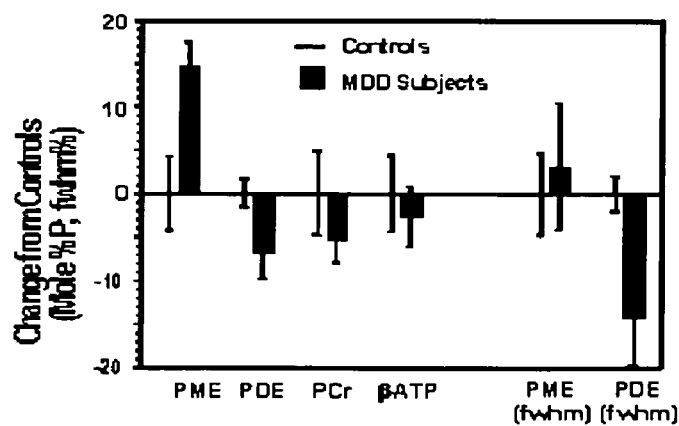
FIG. 6 is a block diagram illustrating a percent change of in vivo 31P MRSI metabolite levels and PME, PDE linewidths

FIG. 6 is a block diagram illustrating a percent change of in vivo $^{31}$P MRSI metabolite levels and PME, PDE linewidths [full width at half maximum (fwhm)] of 2 MDD subjects compared with 13 control subjects.

As part of an ongoing $^{31}$P-$^{1}$H MRSI study of never-medicated, first-episode schizophrenia subjects three $^{31}$P MRSI spectra on 2 MDD subjects (1 Asian male, 1 white female, 24∀2.3 years) were obtained. The MDD spectral results are compared with those obtained from 13 controls (6 males; 3 white, 2 African-American, 1 Asian and 7 females;

4 white, 3 African-American; 21∀1.0 years). PME levels in the MDD subjects were increased by approximately 15% (p=0.13) while there were decreases in the levels of PDE (approx. −7%; p=0.08), PCr (approx. −5%, p=0.61), and β-ATP (approx. −3%, p=0.87) (FIG. 6). Treatment with ALCAR lowered PME levels in the MDD subjects. Of note is that the PDE linewidth is decreased by approximately −15% suggesting the loss of PDE moieties is mostly those with i-$\tau_c$ such as synaptic vesicles. These findings suggest molecular alterations related to both membrane phospholipid and high-energy metabolism in these subjects.

The methods describe herein treat depression and bi-polar depression with ALCAR, thereby avoiding unwanted side-effects exhibited by conventional antidepressant agents. ALCAR also helps prevents recurrent episodes of depression and bi-polar depression.

Molecular Studies of Cognition in Alcoholism

Chronic alcoholism is a diverse and heterogeneous disorder that can be dichotomized into cognitively intact and cognitively impaired subgroups. At a molecular level, ethanol has been shown to have both acute and chronic effects on: (1) Membrane biophysical properties; (2) Membrane composition and metabolism; (3) Protein phosphorylation; (4) Lipid metabolic signaling; and (5) Lipoprotein transport of cholesterol.

Cognitive status was determined by an index from the Halstead-Reitan Battery (HRB). Regionally specific molecular measures distinguish: (1) controls from chronic unimpaired (CUCAL) and impaired (CICAL) subjects; and (2) cognitively unimpaired from cognitively unimpaired alcoholism subjects.

FIG. 7 is a flow diagram illustrating a Method 40 for diagnosing chronic alcoholism in a human. At Step 42, molecular alterations in membrane phospholipid and high-energy phosphate metabolism are examined in a human brain with a medical imaging process. At Step 44, molecular alterations in synaptic transport vesicles are examined with the medical imaging process. At Step 46, molecular alternations in phosphorylated proteins are examined with the medical imaging process. At Step 48, and molecular alterations in metabolites with N-acetyl moieties and gangliosides are examined with the medical imaging process. At Step 50, the plural examined molecular alterations are used to determine if a conclusion of cognitively impaired chronic alcoholism in the human is suggested.

In one embodiment, Method 30 is used to study molecular underpinnings for cognitive impairment observed in some chronic alcoholism subjects using $_{31}P$ $^1H$ magnetic resonance spectroscopic imaging examining molecular alterations in membrane phospholipid and high-energy phosphate metabolism, synaptic/transport vesicles, phosphorylated proteins and molecular alterations in metabolites with N-acetyl moieties, and gangliosides in a chronic alcoholism cohort (N=20; 10 cognitively unimpaired, 10 cognitively impaired) compared to a demographically matched control group (N=10).

However, the present invention is not limited to such a embodiment and imaging and molecular alterations can also be used to practice the invention. A statistical analysis was completed.

SAS PROC GENMOD: This is a Generalized Linear Model in version 8 of SAS software that allows analysis of correlated data arising from repeated measurements when the measurements are assumed to be multivariate. However, the present invention is not limited to using SAS and other statistical packages can also be use. Main effect terms used: Diagnosis, Brain Region, and Age. Interaction terms: Diagnosis * Brain Region. Table 1. illustrates experimental results.

TABLE 1

| Cognitively Unimpaired Alcoholism Subjects | |
|---|---|
| Males: | 5 |
| Mean Age: | 48.2 +/− 8.3 years |
| Average Impairment Rating (AIR) Score: | 1.8 +/− 0.3 |
| Cognitively Impaired Alcoholism Subjects | |
| Males: | 4 |
| Mean Age: | 49.5 +/− 4.0 years |
| AIR Score: | 2.8 +/− 0.3 |
| Control Subjects | |
| Males: | 16 |
| Mean Age: | 40.8 +/− 5.9 years |

Mean Age Comparisons of Study Groups: CICAL vs. Control, p = 0.02; CUCAL vs. Controls, p = 0.03

FIG. 8 is a block diagram 42 of a phosphorous magnetic resonance spectroscopic image illustrating Chronic Alcoholism in Males Cognitively Impaired (N=4) versus Cognitively Unimpaired (N=5) where p<0.0001.

FIG. 9 is a block diagram 44 of a phosphorous magnetic resonance spectroscopic image illustrating Correlations—MRS metabolites versus Neuropsychological Scores (N=9).

FIG. 9 illustrates $(\alpha-\gamma)ATP$ TRA TIME p=0.002, r=0.094, TRB TIME, p=0.006 and r=0.089, TRB time p=0.02, r=(−0.94), $PME(s-\tau_c)$ VIQ p=0.001, r=(−0.92), FSIQ p=0.005, r=(−0.87), NAA/PCr+Cr p=0.002, r=0.98.

The molecular changes found and illustrated in FIGS. 8 and 9 primarily involve membrane repair, with faulty repair processes in individuals with cognitive impairment, predominantly in posterior regions of the brain. These experimental results reveal regional molecular/metabolic alterations of phospholipid and ganglioside metabolism which distinguish cognitively impaired and cognitively unimpaired chronic alcoholism subjects from controls and cognitively impaired from cognitively unimpaired subjects.

FIG. 10 is flow diagram illustrating a Method 46 for diagnosing chronic alcoholism in a human. At Step 48, a human brain is imaged with a medical imaging process. In Step 50, a first signal intensity for membrane phospholipid building blocks including phosphomonoesters ($PME(s-\tau_c)$) is measured in left inferior parietal regions of a human brain. At Step 52, a second signal intensity for synaptic/transport vesicles including phosphodiesters ($PDE(i-\tau_c)$) is measured in right inferior parietal regions of the human brain. At Step 54, a third signal intensity for lipid/protein glycosylation intermediates and membrane phospholipid cofactors (($\alpha-\gamma$)ATP) is measured in a left occipital region of the human brain. At Step 56, a fourth signal intensity for N-acetylaspartate/phosphocreatine+creatine (NAA/PCr+Cr) reflecting increased N-acetylaspartate or N-acetylated sugars is measured in a left superior temporal region of the human brain. At Step 58, determine if a conclusion of cognitively impaired chronic alcoholism in the human is suggested using the plural measurements.

It has been experimentally determined that cognitively impaired (i.e., compared with cognitively unimpaired) chronic alcoholism subjects demonstrate: (1) Increased membrane phospholipid building blocks ($PME(s-\tau_c)$) in left inferior parietal regions of a human brain; (2) Decreased synaptic/transport vesicles ($PDE(i-\tau_c)$) in the right inferior parietal region of the human brain; (3) Increased lipid/protein glycosylation intermediates and membrane phospholipid cofactors (($\alpha-\gamma$)ATP) in the left occipital region of the human brain; and (4) Increased NAA/PCr+Cr reflecting increased N-acetylaspartate or N-acetylated sugars in the left superior temporal region of the human brain.

These findings conclude the cognitively impaired chronic alcoholism subjects have increased neural membrane repair mechanisms which are failing [i.e., ↑ $PME(s-\tau_c)$, ↑($\alpha-\gamma$)ATP, ↑ NAA/PCr+Cr] which is consistent with evidence of loss of synaptic/transport vesicles [⇓ $PDE(i-\tau_c)$].

Neuropsychological—Molecular/Metabolic Correlations. Markers of synaptic/transport vesicles ($PDE(i-\tau_c)$) intermediates in protein, lipid glycosylation, and membrane phospholipid metabolism (($\alpha-\gamma$)ATP) and a measure of neuronal integrity or ganglioside synthesis (NAA/PCr+Cr) correlate with better performance on several neuropsychological measures. This in general reflects repair of synaptic membranes which are enriched in gangliosides which contain sialated sugars. A marker of generalized membrane repair of damaged neural membranes ($PME(s-\tau_c)$), has an inverse correlation with several neuropsychological measures. This suggests that generalized membrane degeneration is a later pathophysiological event than more localized synaptic membrane degeneration in chronic alcoholism.

Compared to controls, the CUCAL subjects had increased measures of phosphomonoesters in the right occipital region, suggesting that neural membrane repair mechanisms are operating in the CUCAL subjects. Compared to controls, the CICAL subjects had: Increased membrane phospholipid building blocks in the left inferior parietal and occipital; decreases in measures of phosphorylated proteins in the right inferior parietal; increases in measures of lipid and protein glycoslyation in the left inferior parietal and occipital; and increases in measures of N-acetylaspartate in the left superior temporal, right basal ganglia, and right inferior parietal regions.

These findings suggest attempts at membrane repair with decreased levels of phosphorylated peptides. Compared to CUCAL subjects CICAL subjects had: (1) increased membrane phospholipids in right superior temporal and left inferior parietal but decreases in right occipital; (2) decreased measures of synaptic vesicles in right inferior parietal; (3) increases in lipid and protein glycoslyation in the left occipital and (4) increased measures of N-acetylaspartate (NAA) or other N-acetylglutamic acids (NAG) in the left superior temporal, right basal ganglia, and right inferior parietal regions. These findings suggest the CICAL subjects have failing membrane repair mechanisms consistent with evidence of loss of synaptic vesicles.

Molecular Studies of Cognition in Schizophrenia

Subjects with schizophrenia illustrate molecular underpinnings for cognitive impairment similar to those observed in some chronic alcoholism subjects. Changes in chronic schizophrenia males (i.e., cognitively impaired versus cognitively unimpaired) demonstrate decreased $PME(s-\tau_c)$ in the right basal ganglia. These findings conclude the cognitively impaired chronic schizophrenia subjects do not have the neural membrane repair mechanisms [i.e., ↑$PME(s-\tau_c)$, ↑$(\alpha-\gamma)$ ATP, ↑ NAA/PCr+Cr] which are seen in the chronic alcoholism subjects. Similarly, changes demonstrated for chronic alcoholism subjects compared with controls are not seen in chronic schizophrenia subjects. A positive correlation of NAA/PCr+Cr with IQ measures in the left superior temporal and a negative correlation of $PME(s-\tau_c)$ with average impairment rating (AIR) in the right superior temporal region in chronic schizophrenia subjects were not seen in chronic alcoholism subjects. A statistical analysis was completed.

SAS PROC GENMOD: This is a Generalized Linear Model in version 8 of SAS software that allows analysis of correlated data arising from repeated measurements when the measurements are assumed to be multivariate. However, the present invention is not limited to using SAS and other statistical packages can also be use. Main effect terms used: Diagnosis, Brain Region, and Age. Interaction terms: Diagnosis * Brain Region. Table 2 illustrates experimental results.

TABLE 2

| Cognitively Unimpaired Schizophrenia Subjects: | |
|---|---|
| Males: | 16 |
| Mean Age: | 42.6 +/− 8.0 years |
| Average Impairment Rating (AIR) Score: | 1.6 +/− 0.5 |
| Cognitively Impaired Schizophrenia Subjects | |
| Males: | 19 |
| Mean Age: | 47.3 +/− 7.5 years |
| AIR Score: | 3.0 +/− 0.3 |
| Control Subjects | |
| Males: | 10 |
| Mean Age: | 42.0 +/− 10.6 years |
| AIR Score: | 1.1 +/− 0.5 |
| Middle Age Smokers | |
| Males (N = 4) Females (N = 4) | |
| Mean Age: | 40.1 +/− 4.0 years |

FIG. 11 is a block diagram 60 of a phosphorous magnetic resonance spectroscopic image illustrating Chronic Schizophrenia (males): Cognitively Impaired (N=19) versus Cognitively Unimpaired (N=16) where p<=0.01.

FIG. 12 is a block diagram 62 of a phosphorous magnetic resonance spectroscopic image illustrating Correlations—MRS Metabolites vs. Neuropsychological Scores (N=35) and illustrates $PME(s-\tau_c)$ AIR, NAA/PCr+Cr FSIQ, VIQ, PIQ, where p<=0.005 and r>0.45.

Subjects with using nicotine do not illustrate the same molecular underpinnings for cognitive impairment observed in some chronic alcoholism subjects.

FIG. 13 is a block diagram 64 of a phosphorous magnetic resonance spectroscopic image illustrating Effects of Nicotine: Middle Age Smokers (N=8), Nicotine vs. Placebo Patch, and illustrates $PME(s-\tau_c)$ and $PDE(i-\tau_c)$ levels where p<0.01.

FIGS. 11-13 illustrate that compared to chronic alcoholism subjects similar metabolic patterns were not observed in chronic schizophrenia subjects (cognitively unimpaired or impaired) and were not observed in middle age smokers after nicotine challenge.

The HRB-based AIR proved to be a valid indicator of metabolic differences between cognitively impaired and unimpaired subjects. Several of the striking molecular findings in the chronic alcoholism subjects are in regions of the brain (basal ganglia and right inferior parietal) that have been implicated by neuropsychological findings of complex motor and visual-spatial deficits.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

It should be understood that the architecture, programs, processes, methods and systems described herein are not related or limited to any particular type of component or compound unless indicated otherwise. Various types of general purpose or specialized components and compounds may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

We claim:

1. A method for diagnosing alcoholism disease in a human, comprising:

examining molecular alterations in membrane phospholipid and high-energy phosphate metabolism in a human brain with a medical imaging process, wherein the medical imaging process is a multinuclear magnetic resonance process based on comparison of intensities obtained from relevant $^{31}$P nuclear magnetic resonance signals obtained from non-alcoholic hosts and known alcoholic hosts with cognitive impairment due to alcohol abuse and with signal information obtained from a new patient with an unknown cognitive condition;

examining molecular alterations in synaptic/transport vesicles with the medical imaging process;

examining molecular alterations in phosphorylated proteins with the medical imaging process;

examining molecular alterations in metabolites with N-acetyl moieties and gangliosides are examined with the medical imaging process; and determining with the plurality of examined molecular alterations whether a conclusion of cognitively impaired chronic alcoholism in the human is suggested if the examined molecular alterations indicate increased neural membrane repair mechanisms which are failing including an increase in phosphomonoesters PME(s-$\tau_c$)), an increase in phospholipid cofactors (($\alpha$-$\gamma$)ATP), an increase in N-acetylaspartate/phosphocreatine+creatine (NAA/PCr+Cr) reflecting increased N-acetylaspartate or N-acetylated sugars and a loss of synaptic/transport vesicles reflecting a decrease in phosphodiesters (PDE(i-$\tau_c$)) in the human brain.

2. The method of claim 1 wherein the molecular alterations in the membrane phospholipid and high-energy phosphate metabolism includes molecular alterations in phosphomonoesters (PME(s-$\tau_c$)) in left inferior parietal regions of the human brain.

3. The method of claim 1 wherein the molecular alterations in synaptic transport vesicles includes molecular alterations in phosphodiesters (PDE(i-$\tau_c$)) in a right inferior parietal region of the human brain.

4. The method of claim 1 wherein the molecular alterations in phosphorylated proteins include molecular alternations in phospholipid cofactors (($\alpha$-$\gamma$)ATP) in a left occipital region of the human brain.

5. The method of claim 1 wherein the molecular alterations in metabolites with N-acetyl moieties and gangliosides include molecular alterations in N-acetylaspartate/phosphocreatine+creatine (NAA/PCr+Cr) reflecting increased N-acetylaspartate or N-acetylated sugars in a left superior temporal region of the human brain.

6. A method for diagnosing alcoholism disease in a human, comprising:

imaging a brain of a human with a medical imaging process, wherein the medical imaging process is a multinuclear magnetic resonance process based on comparison of intensities obtained from relevant $^{31}$P nuclear magnetic resonance signals obtained from non-alcoholic hosts and known alcoholic hosts with cognitive impairment due to alcohol abuse and with signal information obtained from a new patient with an unknown cognitive condition;

determining a first signal intensity for membrane phospholipid building blocks including phosphomonoesters (PME(s-$t_c$)) in left inferior parietal regions of the human brain;

determining a second signal intensity for synaptic/transport vesicles including phosphodiesters (PDE(i-$\tau_c$)) in right inferior parietal regions of the human brain;

determining a third signal intensity for lipidlprotein glycosylation intermediates and membrane including phospholipid cofactors (($\alpha$-$\gamma$)ATP) in left occipital regions of the human brain;

determining a fourth signal intensity for N-acetylaspartate/phosphocreatine+creatine (NAA/PCr+Cr) reflecting increased N-acetylaspartate or N-acetylated sugars in left superior temporal regions of the human brain; and determining whether a conclusion of cognitively impaired chronic alcoholism in the human is suggested if the determined signal intensities determined signal intensities indicate increased neural membrane repair mechanisms which are failing including an increase in phosphomonoesters (PME(s-$\tau_c$)), an increase in phospholipid cofactors (($\alpha$-$\gamma$)ATP), an increase in N-acetylaspartate/phosphocreatine+creatine (NAA/PCr+Cr) reflecting increased N-acetylaspartate or N-acetylated sugars and a loss of synaptic/transport vesicles reflecting a decrease in phosphodiesters (PDE(i-$\tau_c$)) in the human brain.

* * * * *